United States Patent [19]

Albertson

[11] 4,161,598

[45] Jul. 17, 1979

[54] 1-OXYGENATED-2,6-METHANO-3-BENZAZOCINES

[75] Inventor: Noel F. Albertson, Schodack, N.Y.

[73] Assignee: Sterling Drug Inc., New York, N.Y.

[21] Appl. No.: 813,813

[22] Filed: Jul. 8, 1977

Related U.S. Application Data

[63] Continuation-in-part of Ser. No. 406,199, Oct. 15, 1973, abandoned, which is a continuation-in-part of Ser. No. 257,343, May 26, 1972, Pat. No. 3,823,149, which is a continuation-in-part of Ser. No. 43,556, Jun. 4, 1970, abandoned.

[51] Int. Cl.$^2$ .......................................... C07D 221/26
[52] U.S. Cl. ..................................... 546/97; 424/267
[58] Field of Search .................. 260/293.54, DIG. 13; 546/97

[56] References Cited

U.S. PATENT DOCUMENTS 3,639,407  2/1972  Clarke et al. ................... 260/293.54
3,700,734  10/1972  Robinson et al. ............... 260/293.54

OTHER PUBLICATIONS

Wiberg, K., Editor, *Oxidation in Organic Chemistry*, Part A, Academic Press, New York, 1965, pp. 105–106.
Ziering, A., et al., *J. Med. Chem.*, 13, 9–13 (1/1970).
Häfliger, O. et al., *Helv. Chim. Acta*, 39, 2053–2062 (1956).

*Primary Examiner*—John M. Ford
*Assistant Examiner*—Richard A. Schwartz
*Attorney, Agent, or Firm*—Theodore C. Miller; B. Woodrow Wyatt

[57] ABSTRACT

1-Oxygenated-1,2,3,4,5,6-hexahydro-6-alkyl-11-(hydrogen or alkyl)-2,6-methano-3-benzazocines useful as narcotic analgesics and/or strong analgesics are prepared by N-alkylation of the corresponding N-H compounds, 1-oxidation of the corresponding 1-CH$_2$ compounds or O-demethylation of the corresponding 8-methoxy compounds.

18 Claims, No Drawings

1-OXYGENATED-2,6-METHANO-3-BENZAZO-CINES

CROSS-REFERENCE TO RELATED APPLICATIONS

This application is a continuation-in-part of my copending application Ser. No. 406,199, filed Oct. 15, 1973 and now abandoned, which in turn a continuation-in-part of my copending application Ser. No. 257,343, filed May 26, 1972 and now U.S. Pat. No. 3,823,149, which is in turn a continuation-in-part of my application Ser. No. 43,556, filed June 4, 1970 and now abandoned. Application Ser. No. 369,870, filed June 14, 1973, also copending with application Ser. No. 257,343, now U.S. Pat. No. 3,823,149, and also a continuation-in-part thereof, is now U.S. Pat. No. 3,936,462.

BACKGROUND OF THE INVENTION

1. Field of the Invention

This invention relates to 1-oxygenated-1,2,3,4,5,6-hexahydro-6-alkyl-11-(hydrogen or alkyl)-2,6-methano-3-benzazocines and intermediates and processes therefor.

2. Prior Art Statement

The only 1-oxygenated-1,2,3,4,5,6-hexahydro-6-alkyl-11-(hydrogen or alkyl)-2,6-methano-3-benzazocines of the prior art known to me are three compounds described by Ziering (et al., J. Med. Chem. vol. 13, pp. 9–13, 1970) as having in the free base form the structural formulas

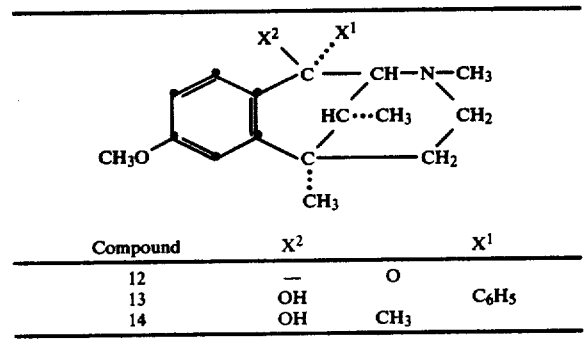

| Compound | $X^2$ | $X^1$ |
|---|---|---|
| 12 | — | O |
| 13 | OH | $C_6H_5$ |
| 14 | OH | $CH_3$ |

The three compounds were prepared primarily as intermediates from which the 1-oxygen functions were removed to provide 1-(phenyl or methyl)-1,2,3,4,5,6-hexahydro-6,11-dimethyl-2,6-methano-3-benzazocines, but were incidentally tested for analgesic, anti-inflammatory and antiedema, and morphine antagonist activity. Compound 12 (as the hydrochloride salt) was inactive in all tests except the morphine antagonist test in the mouse. Before the publication of the Ziering reference, compound 12 (as the free base) was prepared under my direction in my laboratory and was tested for morphine antagonist and meperidine antagonist activity in the rat. The compound was inactive against morphine and weakly active against meperidine and is therefore not a true antagonist. Compounds 13 and 14 are reported by the Ziering reference to be weakly active in the writhing test for analgesia in the mouse, and inactive in all other tests. The Ziering reference states in summary that compounds 12–14 would be of no further interest as analgesics, anti-inflammatories or morphine antagonists. In spite of the conclusion of the Ziering reference and the implication thereof that 1-oxygenation does not produce valuable biological properties in 1,2,3,4,5,6-hexahydro-6-alkyl-11-(hydrogen or alkyl)-2,6-methano-3-benzazocines, I have prepared, or have had others prepare certain new 1-oxygenated 1,2,3,4,5,6-hexahydro-6-alkyl-11-(hydrogen or alkyl)-2,6-methano-3-benzazocines which in fact do have valuable biological properties and which I now describe and claim as my invention.

SUMMARY OF THE INVENTION

In a composition of matter aspect the invention is 3-Q-6-$R^1$-11-$R^2$-1-$Y^1$-1-$Y^2$-8-Z-1,2,3,4,5,6-hexahydro-2,6-methano-3-benzazocine having the structural formula

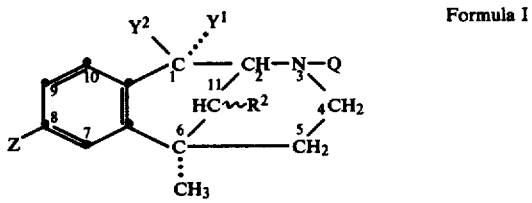

Formula I wherein:

Q is cyclopropylmethyl, cyclobutylmethyl, propyl, allyl or 2-phenylethyl;

$R^1$ is methyl, ethyl or propyl;

$R^2$ is hydrogen, methyl or ethyl;

$Y^1$ taken alone is hydrogen;

$Y^2$ taken alone is hydroxy; or $Y^1$ and $Y^2$ taken together are oxo; and

Z is hydroxy; and when $Y^1$ and $Y^2$ taken together are oxo, Z is also acyloxy selected from the group consisting of acetoxy, propionyloxy, butyryloxy, pivalyloxy, isobutyryloxy, isovaleryloxy, 3,3-dimethylbutanoyloxy, benzoyloxy, p-anisoyloxy, m-anisoyloxy, p-toluyloxy and p-trifluoromethylbenzoyloxy;

or an acid-addition salt thereof.

The compounds of Formula I are useful as analgesics and mostly also useful as narcotic antagonists as shown by tests in experimental animals, and are intended for use in humans as analgesics. One species is being tested in humans as an analgesic.

In another composition of matter aspect, the invention is 6-$R^1$-11-$R^2$-1-$Y^1$-$Y^2$-8-$Z^*$-1,2,3,4,5,6-hexahydro-2,6-methano-3-benzazocine having the structural formula

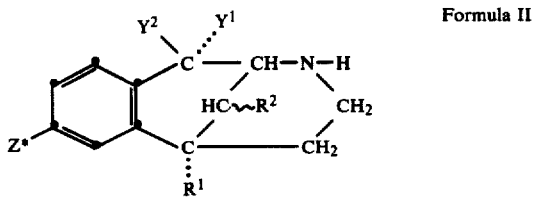

Formula II wherein:

$R^1$ is methyl, ethyl or propyl;

$R^2$ is hydrogen, methyl or ethyl;

$Y^1$ taken alone is hydrogen;

$Y^2$ taken alone is hydroxy; or $Y^1$ and $Y^2$ taken together are oxo; and $Z^*$ is hydroxy or methoxy;

or an acid-addition salt thereof.

The compounds of Formula II are useful as intermediates in preparing the compounds of Formula I.

In a process aspect the invention is the process which comprises oxidizing a compound having the structural formula

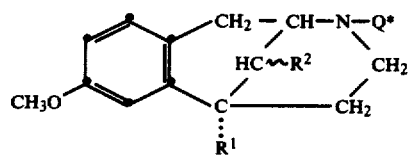

Formula III with a chromium (VI) compound in an acidic medium to form a compound having the structural formula

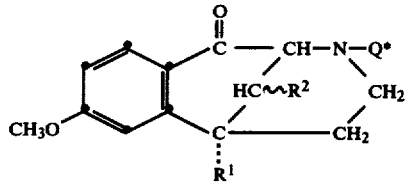

Formula IV wherein:

Q* is hydrogen, methyl, acetyl, cyclopropylmethyl, cyclobutylmethyl, propyl, allyl, or 2-phenylethyl;
$R^1$ is methyl, ethyl or propyl; and
$R^2$ is hydrogen, methyl or ethyl.

The process is useful for preparing the compounds of Formulas I and II.

DETAILED DESCRIPTION OF THE INVENTION

The compounds of Formula I-IV are totally synthetic and, therefore, racemic and the racemates may be resolved into their optical isomers. Each of the formulas represents only one optical isomer of a racemic pair and the mirror image thereof would represent the other optical isomer. The $Y^2$—C feature of Formulas I and II represents a bond oriented above the plane of the page and the C··$Y^1$ feature of Formulas I and II and the C··$R^1$ feature of Formulas I-IV represent bonds oriented below the plane of the page, if the plane of the tetralin moiety is considered to be in the plane of the page. The symbol ~ in the HC~$R^2$ feature of Formulas I-IV represents a bond which can be either cis or trans to the C··$R^1$ bond. The preferred orientation is HC··$R^2$, which is the cis orientation. The trans orientation is represented by HC—$R^2$. With reference to the tetralin moiety, $R^1$, $R^2$ in the trans orientation and $Y^2$ are equatorial and $R^2$ in the cis orientation is axial. If the plane of the tetralin moiety is considered to be in the plane of the page, the piperidine moiety is oriented above the plane of the page.

The compounds of Formula I wherein Z is hydroxy and the compounds of Formula IV where Q* is cyclopropylmethyl, cyclobutylmethyl, propyl, allyl or benzyl (Q* is the same as Q) are prepared by alkylating the corresponding compounds of Formula II with Q-An in the presence of an acid-absorber, wherein An is the anion of any strong organic or inorganic acid which does not interfere with the alkylation, especially halide, for example, chloride or bromide, or arylsulfonate, for example, p-toluenesulfonate. Any effective acid absorber may be used, especially an alkali metal carbonate, for example, sodium bicarbonate. Ordinarily it is preferable to use a diluent such as a lower alkanol, for example, methanol or ethanol, or an N,N-(di-lower alkyl)-lower alkanamide, for example, N,N-dimethylformamide or N,N-dimethylacetamide. The N-alkylation may be carried with or without heating or cooling.

The compounds of Formula I wherein Z is hydroxy are also prepared by O-demethylation of the corresponding compounds having the structural formula

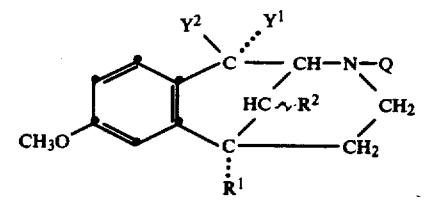

Formula V wherein:

Q is cyclopropylmethyl, cyclobutylmethyl, propyl, allyl or 2-phenylethyl;
$R^1$ is methyl, ethyl or propyl;
$R^2$ is hydrogen, methyl or ethyl;
$Y^1$ taken alone is hydrogen; or
$Y^2$ taken alone is hydroxy; and
$Y^1$ and $Y^2$ taken together are oxo;

with a reagent effective in cleaving the methyl ether bond without affecting any other portion of the molecule, for example, boron tribromide or sodium propylmercaptide. A diluent is preferably used, for example, methylene dichloride in the case of boron tribromide or N,N-dimethylformamide in the case of sodium propylmercaptide. The O-demethylation is usually carried out with cooling and subsequent warming in the case of of boron tribromide or heating in the case of sodium propylmercaptide.

The compounds of Formula I wherein $Y^1$ is hydrogen and $Y^2$ is hydroxy are also prepared by reduction of the corresponding compounds having the structural formula

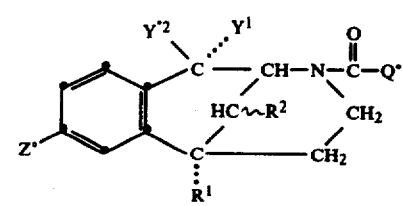

Formula VI wherein:

Q° is cyclopropyl, cyclobutyl, ethyl, vinyl or benzyl;
$R^1$ is methyl, ethyl or propyl;
$R^2$ is hydrogen, methyl or ethyl;
$Y^1$ taken alone is hydrogen;
$Y^{\circ 2}$ taken alone is hydroxy or Q°COO; or
$Y^1$ and $Y^{\circ 2}$ taken together are oxo; and
Z° is hydroxy or Q°COO;

with a reagent effective in reducing N-carbonyl to N-methylene, 1-oxo (if present) to 1-hydroxy, and cleaving the Q°CO—O bond(s) (if present) without affecting any other part of the molecule, for example, lithium aluminum hydride. A diluent is preferably used, for example, tetrahydrofuran. The reduction may be carried out with or without heating or cooling. The compounds of Formula VI are prepared by acylation of the corresponding compounds of Formula II wherein Z* is hydroxy with an active acylating form of the carboxylic acid of Formula Q°COOH such as the acid halide, for example, the acid chloride, the anhydride or a mixed anhydride, for example, the mixed anhydride with trifluoroacetic acid. The acylation may be carried with or without a diluent, with or without an acid absorber and with or without heating or cooling. The diluent and the acid absorber may be the same, for example, pyridine, or different, for example, chloroform and triethylamine respectively.

The compounds of Formula I wherein $Y^1$ and $Y^2$ taken together are oxo and Z is acyloxy are prepared by acylating the corresponding compounds of Formula I wherein $Y^1$ and $Y^2$ taken together are oxo and Z is hydroxy with an active acylating form of the appropriate carboxylic acid such as an acid halide, for example, the acid chloride, the anhydride or a mixed anhydride, for example, the mixed anhydride with trifluoroacetic acid. The acylation may be carried out with or without a diluent, with or without an acid absorber and with or without heating and cooling. The diluent and the acid absorber may be the same, for example, pyridine, or different, for example, sodium methoxide and N,N-dimethylformamide, respectively.

The compounds of Formula III are a known class of compounds.

The compounds of Formula IV are prepared from the corresponding compounds of Formula III in accordance with the process aspect of the invention. The oxidizing medium for the process is prepared by dissolving chromium trioxide in a solution of an inorganic acid such as sulfuric acid or phosphoric acid or in acetic anhydride, trichloroacetic acid or other suitable organic acid, or mixtures thereof. In these media, the chromium (VI) species is chromic acid or a chromyl compound, for example, chromyl sulfate, chromyl phosphate, chromyl acetate or chromyl trifluoroacetate, or mixtures thereof. The oxidation rate is dependent on the structure of the starting material, the particular species of chromium (VI) and the temperature, which is usually controlled in the range of 20°–100° C.

The compounds of Formula IV wherein Q* is hydrogen correspond to the compounds of Formula II wherein $Y^1$ and $Y^2$ taken together are oxo and Z* is methoxy, O-demethylation of which, for example, with hydrobromic acid or boron tribromide affords the corresponding compounds of Formula II wherein $Y^1$ and $Y^2$ taken together are oxo and Z* is hydroxy. N-Demethylation of the compounds of Formula IV wherein Q* is methyl, for example, with cyanogen bromide affords the corresponding compounds of Formula II wherein $Y^1$ and $Y^2$ taken together are oxo and Z* is methoxy.

If a compound of Formula III wherein Q* us acetyl is oxidized according to the process aspect of the invention, the resulting compound of Formula IV wherein Q* is acetyl can be hydrolyzed, for example, with hydrochloric acid to produce the corresponding compound of Formula IV wherein Q* is hydrogen.

Reduction of the compounds of Formula IV wherein Q* is other than acetyl with a reagent effective in reducing 1-oxo to 1-hydroxy, for example, hydrogen over palladium-on-charcoal or platinum oxide or lithium aluminum hydride, affords the corresponding 1-hydroxy compounds having the structural formula

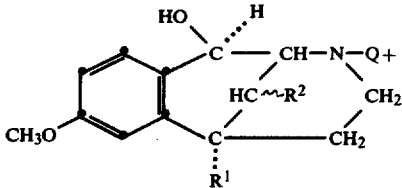

Formula VII wherein:
Q+ is hydrogen, methyl, cyclopropylmethyl, cyclobutylmethyl, propyl, allyl, or 2-phenylethyl;
$R^1$ is methyl, ethyl or propyl; and
$R^2$ is hydrogen, methyl or ethyl.

When Q+ is hydrogen, the compounds of Formula VII correspond to the compounds of Formula II wherein $Y^1$ is hydrogen, $Y^2$ is hydroxy and Z* is methoxy. O-demethylation of the compounds of Formula VII wherein Q+ is hydrogen, for example, with hydrogen bromide or boron tribromide affords the corresponding compounds of Formula II wherein $Y^1$ is hydrogen, $Y^2$ is hydroxy and Z* is hydroxy. N-dimethylation of the compounds of Formula VII wherein Q+ is methyl, for example, with cyanogen bromide affords the corresponding compounds of Formula II wherein $Y^1$ is hydrogen, $Y^2$ is hydroxy and Z* is methoxy. The compounds of Formula VII wherein Q+ is the same as Q correspond to the compounds of Formula V wherein $Y^2$ is hydroxy and $Y^1$ is hydrogen.

The compounds of Formulas I and II are amino bases and react with organic and inorganic acid to form acid-addition salts. Due to the presence of the basic amino grouping, the free base forms represented by Formulas I and II react with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent, and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties of anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic adic, hydriodic acid, perchloric acid, nitric acid, sulfuric acid, phosphoric acid, arsenic acid, and the like. All of the acid-addition salts are useful as sources of the free bases by reaction with a stronger base. Thus, if one or more characteristics such as solubility, molecular weight, physical appearance, toxicity or the like of a given base or acid addition salt thereof render that form unsuitable for the purpose at hand, it can be readily converted to another more suitable form. For pharmaceutical purposes, acid-addition salts of relatively nontoxic, pharmaceutically acceptable acids, for example, hydrochloric acid or methanesulfonic acid, are employed. Either the free bases or the acid-addition salts thereof may crystallize as crystalline solvates.

The following examples illustrate the invention. Structures of products are inferred from known structures of starting materials and analogous processes and are confirmed, and purity of starting materials and products is confirmed, from melting temperature, boiling temperature, elemental analysis, gas-liquid chromatographic analysis, thin-layer chromatographic analysis, infrared spectral analysis, ultraviolet spectral analysis, nuclear magnetic spectral analysis, mass spectral analysis and/or optical rotational analysis.

EXAMPLE 1

A mixture of 9.6 g of 1,2,3,4,5,6-hexahydro-1-oxo-8-hydroxy-6(eq),11(ax)-dimethyl-2,6-methano-3-benzazocine, 5.6 g. of cyclopropylmethyl bromide, 3.5 g. of sodium bicarbonate, and 100 ml. of N,N-dimethylformamide was stirred and refluxed for two hours, and then the reaction mixture was concentrated under reduced pressure. The resulting residue was triturated with water, cooled in ice, and filtered. The white crystalline solid thus collected was washed with water and methyl alcohol and dried. This product, which weighed 8.3 g., was 1,2,3,4,5,6-hexahydro-1-oxo-3-cyclopropylmethyl-8-hydroxy-6(eq),11(ax)-dimethyl-2,6-methano-3-benzazocine. (After crystallization from methyl alcohol, this compound was a white crystalline solid which melted at 249°–252° C.) This base was treated with ethanolic hydrogen chloride to convert it to the hydrochloride, a white crystalline solid which, after recrystallization from ethyl alcohol, melted at 272°–276° C. By treatment of the base with methanesulfonic acid there was obtained the methanesulfonate as a white solid which melted at 257°–258° C.

EXAMPLE 2

A mixture of 10.0 g. of 1,2,3,4,5,6-hexahydro-1-oxo-3-cyclopropylmethyl-8-hydroxy-6(eq),11(ax)-dimethyl-2,6-methano-3-benzazocine and 100 ml. of acetic anhydride was heated and stirred on a steam bath for three hours. The resulting reaction mixture was concentrated and the residue was dissolved in 50 ml. of ethyl acetate and treated with ethereal hydrogen chloride solution. From this mixture there was recovered 11.3 g. of solid which when recrystallized from boiling ethyl acetate yielded 7.6 g. of 1,2,3,4,5,6-hexahydro-1-oxo-3-cyclopropylmethyl-8-acetoxy-6(eq),11(ax)-dimethyl-2,6-methano-3-benzazocine hydrochloride as a white solid which melted at 195°–197° C. The methanesulfonate salt, which was prepared from the base and methanesulfonic acid and purified by washing with ether, melted at 168°–171° C.

EXAMPLE 3

A mixture of 10.0 g. of 1,2,3,4,5,6-hexahydro-1-oxo-3-cyclopropylmethyl-8-hydroxy-6(eq),11(ax)-dimethyl-2,6-methano-3-benzazocine and 100 ml. of propionic anhydride was heated and stirred on a steam-bath for three and one-half hours. The reaction mixture was concentrated under reduced pressure, and the resulting residue was dissolved in 50 ml. of ethyl acetate and treated with ethereal hydrogen chloride solution. From the resulting mixture there was recovered 12.4 g. of solid which when recrystallized from ethyl acetate yielded 8.5 g. of solid which when recrystallized from ethyl acetate yielded 8.5 g. of 1,2,3,4,5,6-hexahydro-1-oxo-3-cyclopropylmethyl-8-propionyloxy-6(eq),11(ax)-dimethyl-2,6-methano-3-benzazocine hydrochloride as a white solid which melted at 187°–188° C.

EXAMPLE 4

To 11.2 g. of 1,2,3,4,5,6-hexahydro-1-oxo-3-cyclopropylmethyl-8-hydroxy-6(eq),11(ax)-dimethyl-2,6-methano-3-benzazocine in 120 ml. of N,N-dimethylformamide there was added 2.4 g. of sodium methoxide. After distilling off 40 ml. of solvent, the mixture was cooled to room temperature, 4.85 g. of butyryl chloride was added dropwise, and the mixture was stirred for one and one-half hours and then allowed to stand overnight. The reaction mixture was concentrated under reduced pressure, the resulting residue was dissolved in 200 ml. of diethyl ether, and the ether solution was shaken quickly with 100 ml. of water. The ether solution was separated, dried, and filtered and the ether was evaporated from the filtrate. The residue thus obtained was dissolved in 50 ml. of ethyl acetate, ethereal hydrogen chloride solution was added, and the solution was cooled. The 8.9 g. of solid which separated in two crops was recrystallized from ethyl acetate to yield 6.3 g. of 1,2,3,4,5,6-hexahydro-1-oxo-3-cyclopropylmethyl-8-butyryloxy-6(eq),11(ax)-dimethyl-2,6-methano-3-benzazocine hydrochloride as a white solid which melted at 195°–197° C.

EXAMPLE 5

Proceeding in a manner similar to that described in Example 4 above, 11.2 g. of 1,2,3,4,5,6-hexahydro-1-oxo-3-cyclopropylmethyl-8-hydroxy-6(eq),11(ax)-dimethyl-2,6-methano-3-benzazocine in 100 ml. of N,N-dimethylformamide was treated with 2.4 g. of sodium methoxide. The resulting product was reacted with 5.3 g. of pivalyl chloride to yield 1,2,3,4,5,6-hexahydro-1-oxo-3-cyclopropylmethyl-8-pivalyloxy-6(eq),11(ax)-dimethyl-2,6-methano-3-benzazocine. This base was converted by treatment with ethereal hydrogen chloride solution to 5.9 g. of the hydrochloride, a white solid which melted at 194°–196° C.

EXAMPLE 6

Proceeding in a manner similar to that described in Example 4 above, 11.2 g. of 1,2,3,4,5,6-hexahydro-1-oxo-3-cyclopropylmethyl-8-hydroxy-6(eq),11(ax)-dimethyl-2,6-methano-3-benzazocine in 100 ml. of N,N-dimethylformamide was treated with 2.4 g. of sodium methoxide. The resulting product was reacted with 4.8 g. of isobutyryl chloride to yield 1,2,3,4,5,6-hexahydro-1-oxo-3-cyclopropylmethyl-8-isobutyryloxy-6(eq),1-1(ax)-dimethyl-2,6-methano-3-benzazocine. This base was converted by treatment with ethereal hydrogen chloride solution to 7.8 g. of the hydrochloride, a white solid which melted at 197°–200° C.

EXAMPLE 7

Proceeding in a manner similar to that described in Example 4 above, 11.2 g. of 1,2,3,4,5,6-hexahydro-1- oxo-3-cyclopropylmethyl-8-hydroxy-6(eq),11(ax)-dimethyl-2,6-methano-3-benzazocine in 100 ml. of N,N-dimethylformamide was treated with 2.4 g. of sodium methoxide. The resulting product was reacted with 5.3 g. of isovaleryl chloride to yield 1,2,3,4,5,6-hexahydro-1-oxo-3-cyclopropylmethyl-8-isovaleryloxy-6(eq),1-1(ax)-dimethyl-2,6-methano-3-benzazocine which was converted by treatment with ethereal hydrogen chloride solution to 6.9 g. of hydrochloride, a white solid which melted at 182°–185° C.

EXAMPLE 8

Proceeding in a manner similar to that described in Example 4 above, 11.2 g. of 1,2,3,4,5,6-hexahydro-1-oxo-3-cyclopropylmethyl-8-hydroxy-6(eq),11(ax)-dimethyl-2,6-methano-3-benzazocine in 100 ml. of N,N-dimethylformamide was treated with 2.4 g. of sodium methoxide. The resulting product was reacted with 5.9 g. of 3,3-dimethylbutanoyl chloride to yield 1,2,3,4,5,6-hexahydro-1-oxo-3-cyclopropylmethyl-8-(3,3-dimethylbutanoyloxy)-6(eq),11(ax)-dimethyl-2,6-methano-3-benzazocine. This base was converted by treatment with ethereal hydrogen chloride solution to 9.8 g. of the hydrochloride, a white solid which melted at 185°–187° C.

EXAMPLE 9

Proceeding in a manner similar to that described in Example 4 above, 11.2 g. of 1,2,3,4,5,6-hexahydro-1-oxo-3-cyclopropylmethyl-8-hydroxy-6(eq),11(ax)-dimethyl-2,6-methano-3-benzazocine in 100 ml. of N,N-dimethylformamide was treated with 2.4 g. of sodium methoxide. The resulting product was reacted with 6.2 g. of benzoyl chloride to yield 1,2,3,4,5,6-hexahydro-1-oxo-3-cyclopropylmethyl-8-benzoyloxy-6(eq),11(ax)-dimethyl-2,6-methano-3-benzazocine. This base was converted by treatment with ethereal hydrogen chloride solution to 5.3 g. of the hydrochloride, a white solid which melted at 190°–191° C.

EXAMPLE 10

Proceeding in a manner similar to that described in Example 4 above, 11.2 g. of 1,2,3,4,5,6-hexahydro-1-oxo-3-cyclopropylmethyl-8-hydroxy-6(eq),11(ax)-dimethyl-2,6-methano-3-benazazocine in 120 ml. of N,N-dimethylformamide was treated with 2.4 g. of sodium methoxide. The resulting product was reacted with 7.5 g. of p-anisoyl chloride to yield 1,2,3,4,5,6-hexahydro-1-oxo-3-cyclopropylmethyl-8-(p-anisoyloxy)-6(eq),11(ax)-dimethyl-2,4-methano-3-benzazocine. This base was converted by treatment with ethereal hydrogen chloride solution to 11.3 g. of the hydrochloride, a white solid which melted at 200°–202° C.

EXAMPLE 11

When m-anisoyl chloride was substituted for the p-anisoyl chloride in the procedure described in Example 10, the product obtained was 5.0 g. of 1,2,3,4,5,6-hexahydro-1-oxo-3-cyclopropylmethyl-8-(m-anisoyloxy)-6(eq),11(ax)-dimethyl-2,6-methano-3-benzazocine hydrochloride, a white solid which melted at 159°–161° C.

EXAMPLE 12

Proceeding in a manner similar to that described in Example 4 above, 11.2 g. of 1,2,3,4,5,6-hexahydro-1-oxo-3-cyclopropylmethyl-8-hydroxy-6(eq),11(ax)-dimethyl-2,6-methano-3-benzazocine in 120 ml. of N,N-dimethylformamide was treated with 2.4 of sodium methoxide. The resulting product was reacted with 6.8 g. of p-toluyl chloride to yield 1,2,3,4,5,6-hexahydro-1-oxo-3-cyclopropylmethyl-8-(p-toluyloxy)-6(eq),11(ax)-dimethyl-2,6-methano-3-benzazocine. This base was converted by treatment with ethereal hydrogen chloride solution to 7.2 g. of the hydrochloride hemi(ethyl acetate), a white solid which melted at 201°–203° C.

EXAMPLE 13

Proceeding in a manner similar to that described in Example 4 above, 11.2 g. of 1,2,3,4,5,6-hexahydro-1-oxo-3-cyclopropylmethyl-8-hydroxy-6(eq),11(ax)-dimethyl-2,6-methano-3-benzazocine in 120 ml. of N,N-dimethylformamide was treated with 2.4 g. of sodium methoxide. The resulting product was reacted with 9.15 g. of p-trifluoromethylbenzoyl chloride to yield 1,2,3,4,5,6-hexahydro-1-oxo-3-cyclopropylmethyl-8-(p-trifluoromethylbenzoyloxy)-6(eq),11(ax)-dimethyl-2,6-methano-3-benzazocine. This base was converted by treatment with ethereal hydrogen chloride solution to 9.7 g. of the hydrochloride, a white solid which melted at 226°–229° C.

EXAMPLE 14

Proceeding in a manner similar to that described above in part A of Example 1, 24.5 g. of 1,2,3,4,5,6-hexahydro-1-oxo-8-methoxy-6(eq),11(ax)-dimethyl-2,6-methano-3-benzazocine was interacted with 9.0 g. of cyclopropylmethyl chloride in the presence of 8.4 g. of sodium bicarbonate and 250 ml. of N,N-dimethylformamide to yield 25 g. of crude 1,2,3,4,5,6-hexahydro-1-oxo-3-cyclopropylmethyl-8-methoxy-6(eq),11(ax)-dimethyl-2,6-methano-3-benzazocine which was converted to 22.0 g. of the crude base hydrochloride, m.p. 187°–190° C. Two recrystallizations of this salt from ethyl alcohol-diethyl ether yielded 12.2 g. of 1,2,3,4,5,6-hexahydro-1-oxo-3-cyclopropylmethyl-8-methoxy-6(eq),11(ax)-dimethyl-2,6-methano-3-benzazocine hydrochloride as a white solid white melted at 192°–193° C.

EXAMPLE 15

A mixture of 9.24 g. of 1,2,3,4,5,6-hexahydro-1-oxo-8-hydroxy-6(eq),11(ax)-dimethyl-2,6-methano-3-benzazocine, 7.48 g. of n-propyl iodide, 3.36 g. of sodium bicarbonate, and 100 ml. of N,N-dimethylformamide was stirred and refluxed for six and one-quarter hours. The reaction mixture was concentrated under reduced pressure and then water and diethyl ether were added. Some of the residue failed to dissolve. The mixture was filtered to collect the crystalline solid which separated from solution. The ether layer and the aqueous layer of the filtrate were separated and the ether layer was evaporated under reduced pressure to yield a further crop of solid which was collected by filtration and washed with water. The two crops of crystalline solid were combined with the undissolved residue from the reaction mixture, and these combined solids were taken up in boiling ethyl alcohol and treated with decolorizing charcoal and the solution was filtered while hot. The filtrate was cooled and the solid which separated from solution was collected on a filter, washed with cold ethyl alcohol, and dried under reduced pressure at 50° C. for three hours. There was thus obtained 8.0 g. of solid which melted at 218°–221° C. The mother liquor from this crystallization was concentrated under reduced pressure to yield a crystalline solid which was collected on a filter, washed with cold ethyl alcohol and dried at 70° C. There was thus obtained a second crop of product weighing 1.15 g. which melted at 214°-218° C. These two crops were combined and recrystallized from ethyl alcohol and dried overnight at 70° C. There was thus obtained 7.0 g. of 1,2,3,4,5,6-hexahydro-1-oxo-3-propyl-8-hydroxy-6(eq),11(ax)-dimethyl-2,6-methano-3-benzazocine as an off-white solid which melted at 219°-222° C.

EXAMPLE 16

A mixture of 4.63 g. of 1,2,3,4,5,6-hexahydro-1-oxo-8-hydroxy-6(eq),11(ax)-dimethyl-2,6-methano-3-benzazocine, 2.5 g. of sodium bicarbonate and 50 ml. of N,N-dimethylformamide was stirred, and 2.66 g. of allyl bromide was added, using 10 ml. of N,N-dimethylformamide to rinse in the residual portion of allyl bromide. The reaction mixture was stirred for fifteen minutes at room temperature and then refluxed for one and one-half hours. The mixture was cooled and filtered and the filtrate was concentrated under reduced pressure. The resulting residue was taken up in a mixture of water and ethyl acetate, and the aqueous layer was separated and extracted with ethyl acetate. The ethyl acetate extract was combined with the ethyl acetate layer and washed with water, treated with decolorizing charcoal, and filtered. The filtrate was concentrated under reduced pressure and the crystalline residue thus obtained was washed with benzene. This product was 1,2,3,4,5,6-hexahydro-1-oxo-3-allyl-8-hydroxy-6(eq),11(ax)-dimethyl-2,6-methano-3-benzazocine. The aqueous layer was concentrated to dryness and the residue was taken up in a mixture of water and diethyl ether. The ether layer was separated, dried, and concentrated under reduced pressure. The resulting oily residue was a second crop of the desired base. Both crops of the base were converted to the hydrochloride by treatment with ethereal hydrogen chloride. The two crops of hydrochloride (2 g.) were combined and recrystallized from isopropyl alcohol and dried overnight under reduced pressure at 60° C. There was thus obtained 1.4 g. of 1,2,3,4,5,6-hexahydro-1-oxo-3-allyl-8-hydroxy-6(eq),11 (ax)-dimethyl-2,6-methano-3-benzazocine hydrochloride as a white solid which melted at 251.0°-252.0° C. (dec.)(corr.).

EXAMPLE 17

To a stirred mixture of 5.0 g. of 1,2,3,4,5,6-hexahydro-1(eq),8-dihydroxy-6(eq),11(ax)-dimethyl-2,6-methano-3-benzazocine, 3.5 g. of sodium bicarbonate, and 60 ml. of N,N-dimethylformamide there was added dropwise a solution of 3.2 g. of allyl bromide in 17 ml. of N,N-dimethylformamide. The mixture was stirred and refluxed for three and one-quarter hours, filtered, and the solid thus collected was rinsed with methyl alcohol. The filtrate, including the methanolic wash liquor, was concentrated under reduced pressure. The residue thus obtained was taken up in a mixture of dilute ammonium hydroxide and chloroform. The chloroform and aqueous layers were separated and the aqueous layer was extracted with chloroform, and the chloroform extract was combined with the chloroform layer, washed with water, dried, treated with decolorizing charcoal, and filtered. The filtrate was concentrated under reduced pressure to yield 9.1 g. of a dark oil. This oil was dissolved in 10 ml. of acetone and the solution was concentrated under reduced pressure to yield 7.0 g. of oil. This oil was chromatographed on 350 g. of silica, eluting with chloroform-methanol-isopropylamine. The collected fraction of product was concentrated under reduced pressure to yield 5.2 g. of solid which was recrystallized from diethyl ether-hexane mixture and dried overnight at 70° C. There was thus obtained 2.8 g. of solid which melted at 144°-148° C. When this product was recrystallized from hexane-acetone mixture there was obtained 1.4 g. of 1,2,3,4,5,6-hexahydro-1(eq),8-dihydroxy-3-allyl-6(eq),11(ax)-dimethyl-2,6-methano-3-benzazocine as a white solid which melted at 148°-150° C.

EXAMPLE 18

A solution of 15.26 g. of 1,2,3,4,5,6-hexahydro-1-oxo-3-cyclopropanecarbonyl-8-cyclopropanecarbonyloxy-6(eq),11(ax)-dimethyl-2,6-methano-3-benzazocine in 100 ml. of tetrahydrofuran was added dropwise to 4.5 g. of lithium aluminum hydride covered with 50 ml. of tetrahydrofuran. The reaction mixture was refluxed for four hours and then cooled and 9.0 ml. of water was added. The mixture was diluted to a volume of 1200 ml. with tetrahydrofuran, diatomaceous silica was added, and the mixture was boiled for ten minutes and filtered. The residue thus collected was washed with hot tetrahydrofuran and the filtrate including the tetrahydrofuran wash liquor was concentrated under reduced pressure to yield 15.0 g. of oily residue. The residue was treated with ethereal hydrogen chloride and the solid which precipitated was collected on a filter, washed with diethyl ether, and dried at 70° C. The filtrate was concentrated under reduced pressure to yield 2.2 g. of solid which was recrystallized three times from ethyl alcohol-diethyl ether mixture and then from isopropyl alcohol-diethyl ether mixture. There was thus obtained 2.0 g. of 1,2,3,4,5,6-hexahydro-1(eq),8-dihydroxy-3-cyclopropylmethyl-6(eq), 11(ax)-dimethyl-2,6-methano-3-benzazocine hydrochloride as an off-white solid which melted at 230.0°-231.0° C. (dec.)(corr.).

EXAMPLE 19

A solution of 26.8 g. of 1,2,3,4,5,6-hexahydro-8-methoxy-6(eq),11(ax)-dimethyl-2,6-methano-3-benzazocine hydrochloride in 500 ml. of 0.5 M sulfuric acid was stirred at 40°-50° C., and to this solution there was added dropwise over a period of four hours a solution of 13.2 g. of chromium trioxide in 500 ml. of 0.5 M sulfuric acid. During this addition a precipitate appeared and then dissolved in the reaction mixture. After addition of the chromium trioxide solution was completed, the reaction mixture was stirred at 40°-50° C. for four and one-half hours and then allowed to stand overnight at room temperature. There was then added to the reaction mixture a solution of 15 g. of sodium bisulfite in 50 ml. of water, followed by the dropwise addition of a solution of 138 g. of potassium carbonate in 500 ml. of water. There was added 50 ml. of concentrated ammonium hydroxide and the mixture was shaken with 500 ml. of chloroform. Diatomaceous silica was added, the mixture was filtered, and the aqueous and chloroform layers in the filtrate were separated. The aqueous layer was extracted with two 500 ml. portions of chloroform and these chloroform extracts were added to the chloroform solution and the combined solution was dried and then concentrated to yield a residue which weighed 25.5 g. This residue was taken up in 300 ml. of anhydrous diethyl ether and there was added dropwise with stirring dilute ethereal hydrogen chloride solution until precipitation was completed. The mixture was stored for two days in a refrigerator and was then filtered to collect the precipitated solid. The product thus collect was washed with ether and dried under reduced pressure for two hours at 60° C. There was thus obtained 20.3 g. of solid which melted at 262°–265° C. This product, which was 1,2,3,4,5,6-hexahydro-1-oxo-8-methoxy-6(eq),11(ax)-dimethyl-2,6-methano-3-benzazocine hydrochloride, melted at 266.0°–268.0° C. (dec.) (corr.) when recrystallized from anhydrous ethanol. Treatment of this hydrochloride with concentrated ammonium hydroxide yielded the corresponding free base.

EXAMPLE 20

A mixture of 43.6 g. of 1,2,3,4,5,6-hexahydro-1-oxo-8-methoxy-6(eq),11(ax)-dimethyl-2,6-methano-3-benzazocine hydrochloride and 200 ml. of 48% hydrobromic acid was refluxed for five hours. The reaction mixture was concentrated under reduced pressure, isopropyl alcohol was added, the mixture was made basic by the addition of ammonium hydroxide and then further concentrated under reduced pressure and cooled. The solid which separated from solution was recrystallized from methyl alcohol and dried overnight at 70° C. There was thus obtained 29.5 g. of solid which melted at 271°–272° C. A 5 g. portion of this solid was recrystallized from N,N-dimethylformamide to yield 3 g. of 1,2,3,4,5,6-hexahydro-1-oxo-8-hydroxy-6(eq),11(ax)-dimethyl-2,6-methano-3-benzazocine as an off-white solid which melted at 272.0°–274.0° C.(dec.)(corr.).

EXAMPLE 21

A. A mixture of 76.8 g. of 1,2,3,4,5,6-hexahydro-8-hydroxy-6(eq),11(eq)-dimethyl-2,6-methano-3-benzazocine and 225 ml. of acetic anhydride was stirred. The mixture became warm and the nor-base dissolved, and a solid reaction product separated from solution. The reaction mixture was heated on a steam bath for one hour and was then filtered. The solid thus collected was washed with ether and dried under reduced pressure at 70° C. over sodium hydroxide. There was thus obtained 74.1 g. of 1,2,3,4,5,6-hexahydro-8-acetoxy-3-acetyl-6(eq),11(eq)-dimethyl-2,6-methano-3-benzazocine as a crystalline solid which melted at 196°–201° C. A small additional amount of this product was recovered by concentrating the filtrate. The combined crops were mixed with a solution of 17 g. of sodium hydroxide and 350 ml. of water and the mixture was stirred and heated on a steam bath for one hour to saponify the ester, 100 ml. of ethyl alcohol was added and stirring the heating were continued. There was added to the mixture dropwise 50 ml. of dimethyl sulfate, and the reaction mixture was stirred for five hours. The mixture was extracted twice with diethyl ether and the ether extracts were combined and washed successively with 25% aqueous sodium hydroxide solution, diluted hydrochloric acid, and water. The ether solution was then dried and concentrated under reduced pressure to yield 74.9 g. of 1,2,3,4,5,6-hexahydro-3-acetyl-8-methoxy-6(eq), 11(eq)-dimethyl-2,6-methano-3-benzazocine as a yellow syrup. A mixture of this syrup and 500 ml. of glacial acetic acid was stirred and there was added in one portion a mixture of 36 g. of chromium trioxide and 150 ml. of water. The resulting mixture, the temperature of which rose to 70° C., was stirred for one hour, then heated on a steam bath for one hour, cooled, and concentrated under reduced pressure. The resulting residue was taken up in a mixture of ether and an aqueous solution containing 10 g. of sodium bisulfite. This mixture was extracted with diethyl ether and the ether solution was dried and filtered and the filtrate was concentrated under reduced pressure to yield 67.3 g. of 1,2,3,4,5,6-hexahydro-1-oxo-3-acetyl-8-methoxy-6(eq),11(eq)-dimethyl-2,6-methano-3-benzazocine as a syrup. (See also Example 21E below).

B. A mixture of 67.3 g. of 1,2,3,4,5,6-hexahydro-1-oxo-3-acetyl-8-methoxy-6(eq),11(eq)-dimethyl-2,6-methano-3-benzazocine, 140 ml. of concentrated hydrochloric acid, and 280 ml. of water was stirred and refluxed for four and one-half hours. The reaction mixture was cooled and the solid which had separated from solution was collected on a filter, washed with methyl alcohol, and dried to yield 47.7 g. of crude 1,2,3,4,5,6-hexahydro-1-oxo-8-methoxy-6(eq),11(eq)-dimethyl-2,6-methano-3-benzazocine hydrochloride. Recrystallization of 3.0 g. of this product twice from methanol yielded 1.2 g. of the pure product as a white solid which melted at 285° C. (dec.).

C. Proceeding in a manner similar to that described above in Example 20, 29.4 g. of 1,2,3,4,5,6-hexahydro-1-oxo-8-methoxy-6(eq),11(eq)-dimethyl-2,6-methano-3-benzazocine was heated with 300 ml. of 48% hydrobromic acid to yield 29.4 g. of 1,2,3,4,5,6-hexahydro-1-oxo-8-hydroxy-6(eq),11(eq)-dimethyl-2,6-methano-3-benzazocine hydrobromide. By dissolving 17.9 g. of the hydrobromide in hot water, adding ammonium hydroxide to the solution, and recrystallizing the resulting precipitate from a mixture of 45 ml. each of water and N,N-dimethylformamide there was obtained 9.0 g. of 1,2,3,4,5,6-hexahydro-1-oxo-8-hydroxy-6(eq),11(eq)-dimethyl-2,6-methano-3-benzazocine as an off-white solid which melted at 258°–259° C.

D. A mixture of 1,2,3,4,5,6-hexahydro-1-oxo-8-methoxy-6(eq),11(ax)-dimethyl-2,6-methano-3-benzazocine and 60 ml. of acetic anhydride was allowed to stand overnight at room temperature (approximately 25° C.). The reaction mixture was evaporated to dryness under reduced pressure, the resulting residue was dissolved in 70 ml. of ethyl alcohol, and the solution was cooled. The solid which separated from solution was collected on a filter, washed with ethyl alcohol, and air-dried. This product weighed 5.8 g. and melted at 121°–123° C. A further crop of solid weighing 7.3 g. and melting at 121°–123° C. was recovered from the filtrate. The two crops were combined and recrystallized from ethyl acetate to yield 8.8 g. of 1,2,3,4,5,6-hexahydro-1-oxo-3-acetyl-8-methoxy-6(eq),11(ax)-dimethyl-2,6-methano-3-benzazocine as a white solid which melted at 122°–124° C.

E. When the corresponding 6 (eq),11(eq)-dimethyl isomer was used as the starting material, N-acetylation yielded 1,2,3,4,5,6-hexahydro-1-oxo-3-acetyl-8-methoxy-6(eq),11(eq)-dimethyl-2,6-methano-3-benzazocine as a white solid which melted at 121°–124° C.

F. By mixing each of the products of parts A and B above with boron tribromide in ethylene chloride at 0° C. and allowing the mixture in each instance to warm to room temperature, there are obtained the corresponding 8-hydroxy compounds.

EXAMPLE 22

To a mixture of 9.25 g. of 1,2,3,4,5,6-hexahydro-1-oxo-8-hydroxy-6(eq),11(ax)-dimethyl-2,6-methano-3-benzazocine and 130 ml. of pyridine there was added dropwise with stirring a solution of 8.36 g. of cyclopropanecarbonyl chloride in 17 ml. of anhydrous diethyl ether. The reaction mixture was stirred for four hours and then allowed to stand overnight. The mixture was then concentrated under reduced pressure and the resulting residue was taken up in a mixture of water and diethyl ether. The aqueous and ether layers were separated, and the ether layer was washed first with 100 ml. of 4.2 M hydrochloric acid and then with water, dried, and concentrated under reduced pressure. There was thus obtained 15.26 g. of 1,2,3,4,5,6-hexahydro-1-oxo-3-cyclopropanecarbonyl-8-cyclopropanecarbonyloxy-6(eq),11(ax)-dimethyl-2,6-methano-3-benzazocine as a glassy oil. By treatment with weak base, such as sodium bicarbonate solution, this esteramide is converted to 1,2,3,4,5,6-hexahydro-1-oxo-3-cyclopropanecarbonyl-8-hydroxy-6(eq),11(ax)-dimethyl-2,6-methano-3-benzazocine.

EXAMPLE 23

A mixture of 27.3 g. of 1,2,3,4,5,6-hexahydro-1-oxo-8-methoxy-6(eq),11(ax)-dimethyl-2,6-methano-3-benzazocine and 800 ml. of glacial acetic acid was catalytically hydrogenated in the presence of 10% palladium-on-charcoal catalyst at room temperature. The reaction mixture was filtered and the filtrate was concentrated under reduced pressure to yield a glassy residue. This residue was taken up in acetone and the acetone solution was cooled for one hour in an ice bath. The solid which had separated from solution was collected on a filter, washed twice with diethyl ether and dried overnight at 70° C. There was thus obtained 19.5 g. of 1,2,3,4,5,6-hexahydro-1(eq)-hydroxy-8-methoxy-6(eq),11(ax)-dimethyl-2,6-methano-3-benzazocine acetate which melted at 180°-182° C. From the filtrate there was recovered an additional 8.0 g. of the product which melted at 174°-176° C.

A 5.0 g. sample of this acetate was dissolved in water and 1 N sodium hydroxide solution was added to cause separation of the free base, 1,2,3,4,5,6-hexahydro-1(eq)-hydroxy-8-methoxy-6(eq),11(ax)-dimethyl-2,6-methano-3-benzazocine. The mixture was extracted with diethyl ether and the extract was dried and filtered, and the filtrate was acidified with ethanolic hydrogen chloride solution, thereby causing separation of an oil which crystallized rapidly. This solid was collected on a filter, washed with diethyl ether and dried at 70° C. This solid, which weighed 4.2 g. and melted at 216°-218° C., was recrystallized from ethyl alcohol-diethyl ether and then from ethyl alcohol-acetone and dried at 70° C. to yield 2.0 g. of 1,2,3,4,5,6-hexahydro-1(eq)-hydroxy-8-methoxy-6(eq),11(ax)-dimethyl-2,6-methano-3-benzazocine hydrochloride as a white solid which melted at 219.0°-220.8° C. (corr.).

This same hydrochloride was obtained by catalytic hydrogenation of 1,2,3,4,5,6-hexahydro-1-oxo-8-methoxy-6(eq), 11(ax)-dimethyl-2,6-methano-3-benzazocine hydrochloride in ethanol in the presence of platinum oxide hydrogenation catalyst; but reduction of the hydrochloride failed when 10% palladium-on-charcoal hydrogenation catalyst was used.

EXAMPLE 24

Following a procedure similar to that described above in Example 19, 56.5 g. of 1,2,3,4,5,6-hexahydro-8-methoxy-6(eq)-ethyl-11(ax)-methyl-2,6-methano-3-benzazocine hydrochloride was oxidized by treatment with 26.4 g. of chromic oxide in dilute sulfuric acid to yield 42.3 g. of 1,2,3,4,5,6-hexahydro-1-oxo-8-methoxy-6(eq)-ethyl-11(ax)-methyl-2,6-methano-3-benzazocine, a white solid which melted at 273°-274° C. By refluxing this product with 450 ml. of 48% hydrobromic acid in a manner similar to that described above in Example 20, there was obtained 37.4 g. of 1,2,3,4,5,6-hexahydro-1-oxo-8-hydroxy-6-(eq)-ethyl-11(ax)-methyl-2,6-methano-3-benzazocine, m.p. 276°-279° C. which was recrystallized from N,N-dimethylformamide to yield 29.7 g. of the product, m.p. 279°-280° C.; and a 10 g. portion of the latter was recrystallized again to yield 9.4 g. of the pure compound as a pale pink solid, m.p. 282°-284° C.

The (−)-cis isomer, prepared by similar oxidation and hydrolysis of (−)cis 1,2,3,4,5,6-hexahydro-8-methoxy-6(eq)-ethyl-11(ax)-methyl-2,6-methano-3-benzazocine hydrochloride, was obtained in the form of pale gray crystals, m.p. 275°-278° C., $[\alpha]_D^{25} = -36.2°$ (2% glacial acetic acid).

EXAMPLE 25

A. Into a stirred solution of 3.2 g. of 1,2,3,4,5,6-hexahydro-3-cyclopropylmethyl-8-methoxy-6(eq),11(ax)-dimethyl-2,6-methano-3-benzazocine in dilute sulfuric acid (prepared by diluting 5 ml. of concentrated sulfuric acid to a volume of 50 ml. with water) there was dripped rapidly at room temperature a solution of 1.3 g. chromium trioxide in 50 ml. of dilute sulfuric acid (prepared in the same manner as before). The resulting reaction mixture was stirred for two hours on a steam bath, and then cooled and 30 ml. of concentrated ammonium hydroxide was added. The mixture was extracted with diethyl ether and the ether extract was dried and concentrated to yield 2.6 g. of crude 1,2,3,4,5,6-hexahydro-1-oxo-3-cyclopropylmethyl-8-methoxy-6(eq),11-(ax)-dimethly-2,6-methano-3-benzazocine as an oil. A 1.4 g. portion of this base was dissolved in diethyl ether and ethanolic hydrogen chloride was added to yield 1.5 g. of 1,2,3,4,5,6-hexahydro-1-oxo-3-cyclopropylmethyl-8-methoxy-6(eq),11(ax)-dimethyl-2,6-methano-3-benzazocine hydrochloride as a white solid which melted at 193°-196° C. (dec.) When a sample of this product was mixed with a sample of the product obtained as described above in Example 14 there was no depression of the melting point.

B. A solution of 0.7 g. of 1,2,3,4,5,6-hexahydro-2,6-oxo-3-cyclopropylmethyl-8-methoxy-6(eq),11(ax)-dimethyl-2,6-methano-3-benzazocine hydrochloride was cooled in an acetone-solid carbon dioxide bath and a solution of 0.52 g. of boron tribromide in 1 ml. of methylene dichloride was added. The resulting reaction mixture was allowed to warm gradually to room temperature and stand for five days. Then the solvent was removed by evaporation, 5 ml. of ice water was added to the residue, and the solid was collected by filtration and dried. This product (0.6 g.; m.p. 187°-193° C.) was recrystallized from water to yield 0.5 g. of 1,2,3,4,5,6-hexahydro-1-oxo-3-cyclopropylmethyl-8-hydroxy-6(eq),11(ax)-dimethyl-2,6-methano-3-benzazocine hydrochloride as a white solid which melted at 194°-200° C. This salt was treated with ammonium hydroxide to yield 0.3 g. of 1,2,3,4,5,6-hexahydro-1-oxo-3-cyclopropylmethyl-8-hydroxy-6(eq),11(ax)-dimethyl-2,6-methano-3-benzazocine as a white solid which melted at 243°-247° C. When a sample of this product was mixed with a sample of the same base prepared as described above in part A of Example 1, there was no depression of the melting point, and the two samples had identical infrared spectra.

EXAMPLE 26

A. Following a procedure similar to that described above in Example 19, 27.1 g. of 2R,6R,11R-1,2,3,4,5,6-hexahydro-8-methoxy-6(eq),11(ax)-dimethyl-2,6-methano-3-benzazocine hydrochloride $[\alpha]_D^{25} -41.5°$ (1% in ethanol), (obtained by resolution of the racemic base with d(+)-tartaric acid and converting the levo-rotatory tartrate via the corresponding base to the base hydrochloride) in 500 ml. of dilute sulfuric acid was oxidized by treatment with a solution of 13.4 g. of chromium trioxide in 500 ml. of dilute sulfuric acid to yield 20.5 g. of 2S,6R,11R-1,2,3,4,5,6-hexahydro-1-oxo-8-methoxy-6(eq),11(ax)-dimethyl-2,6-methano-3-benzazocine. A 1.5 g. portion of this product was converted to the hydrochloride, which was a white solid, m.p. 254°–257° C.; $[\alpha]_D^{25} +8.4°$ (1% in ethanol).

B. A mixture of 19.0 g. of 2S,6R,11R-1,2,3,4,5,6-hexahydro-1-oxo-8-methoxy-6(eq),11(ax)-dimethyl-2,6-methano-3-benzazocine and 100 ml. of 48% hydrobromic acid was refluxed for five hours and allowed to stand at room temperature overnight. From this reaction mixture, after making it basic by addition of ammonium hydroxide, there was isolated 4.9 g. of 2S,6R,11R-1,2,3,4,5,6-hexahydro-1-oxo-8-hydroxy-6(eq),11(ax)-dimethyl-2,6-methano-3-benzazocine, a white solid which melted at 261°–270° C. A small portion of this product was recrystallized from methyl alcohol as a white solid, m.p. 268°–269° C., $[\alpha]_D^{25}+95.8°$ (1% in ethanol).

C. Following a procedure similar to that described above in part A of Example 1, 4.4 g. of 2S,6R,11R-1,2,3,4,5,6-hexahydro-1-oxo-8-hydroxy-6(eq),11(ax)-dimethyl-2,6-methano-3-benzazocine was interacted with 2.5 g. of cyclopropylmethyl bromide in the presence of 1.6 g. of sodium bicarbonate in 40 ml. of N,N-dimethylformamide to yield 2.3 g. of 2S,6R,11R-1,2,3,4,5,6-hexahydro-1-oxo-3-cyclopropylmethyl-8-hydroxy-6(eq),11(ax)-dimethyl-2,6-methano-3-benzazocine as an off-white solid, m.p. 187°–189° C., $[\alpha]_D^{25}-3.7°$ (1% in ethanol). The hydrochloride salt, which was prepared from the base and hydrochloric acid and recrystallized, first from isopropyl alcohol and then from water, melted at 229°–232° C. and showed $[\alpha]_D^{25} = -41.1°$ (1% in ethanol). The methanesulfonate salt, which was prepared from the base and methanesulfonic acid acid and purified by slurrying in isopropyl acetate, melted at 220°–222° C. and showed $[\alpha]_D^{25} = -38.6°$ (1% in water).

D. Following a procedure similar to that described above in parts A–C of this example there was prepared dextro-rotatory 2S,6R,11R-1,2,3,4,5,6-hexahydro-1-oxo-3-cyclopropylmethyl-8-hydroxy-6(eq),11(ax)-dimethyl-2,6-methano-3-benzazocine. The hydrochloride salt, which was prepared from the base and hydrochloric acid, melted at 232°–235° C. and showed $[\alpha]_D^{25} = +40.0°$ (1% in ethanol). The methanesulfonate salt, which was prepared from methanesulfonic acid and purified by slurrying in isopropyl acetate, melted at 220°–222° C. and showed $[\alpha]_D^{25} = +40.8°$ (1% in water)

EXAMPLE 27

Proceeding in a manner similar to that described above in part A of Example 1, 18.7 g. of 1,2,3,4,5,6-hexahydro-1-oxo-8-hydroxy-6(eq),11(eq)-dimethyl-2,6-methano-3-benzazocine hydrobromide was interacted with 8.1 g. of cyclopropylmethyl bromide in the presence of 10.1 g. of sodium bicarbonate in 150 ml. of N,N-dimethylformamide to yield 17 g. of crude 1,2,3,4,5,6-hexahydro-1-oxo-3-cyclopropylmethyl-8-hydroxy-6(eq),11(eq)-dimethyl-2,6-methano-3-benzazocine. This base was converted to its hydrochloride and purified by repeated recrystallization from ethyl alcohol. There was thus obtained 5.4 g. of 1,2,3,4,5,6-hexahydro-1-oxo-3-cyclopropylmethyl-8-hydroxy-6(eq),1-1(eq)-dimethyl-2,6-methano-3-benzazocine hydrochloride hemiethanolate, $(C_{18}H_{23}NO_2.HCl)_2.C_2H_5OH$, as a white solid which melted at 257°–269° C. (dec.).

EXAMPLE 28

A. Following a procedure similar to that described above in Example 19, 73.6 g. of 1,2,3,4,5,6-hexahydro-8-methoxy-6(eq)-ethyl-2,6-methano-3-benzazocine hydrochloride in 1 liter of dilute sulfuric acid was oxidized by treatment with a solution of 38.0 g. of chromium trioxide in 1 liter of dilute sulfuric acid, the reaction mixture thus obtained was made basic by addition of ammonium hydroxide, and then there was isolated from the reaction mixture 52.6 g. of crude 1,2,3,4,5,6-hexahydro-1-oxo-8-methoxy-6(eq)-ethyl-2,6-methano-3-benzazocine. This product was converted to the hydrochloride which was purified to yield 46.8 g. of 1,2,3,4,5,6-hexahydro-1-oxo-8-methoxy-6(eq)-ethyl-2,6-methano-3-benzazocine hydrochloride, m.p. 246°–248° C.

B. By hydrolysis with 460 ml. of 48% hydrobromic acid and basifying the hydrolysis product with ammonium hydroxide, 45.8 g. of 1,2,3,4,5,6-hexahydro-1-oxo-8-methoxy-6(eq)-ethyl-2,6-methano-3-benzazocine hydrochloride was converted to 26.3 g. of 1,2,3,4,5,6-hexahydro-1-oxo-8-hydroxy-6(eq)-ethyl-2,6-methano-3-benzazocine as an off-white solid, m.p. 282°–284° C.

C. Proceeding in a manner similar to that described above in part A of Example 1, 23.1 g. of 1,2,3,4,5,6-hexahydro-1-oxo-8-hydroxy-6(eq)-ethyl-2,6-methano-3-benzazocine was interacted with 13.0 g. of cyclopropylmethyl bromide in the presence of 8.4 g. of sodium bicarbonate in 230 ml. of N,N-dimethylformamide. After the reaction product was treated with ethereal hydrogen chloride, there was obtained 12.8 g. of 1,2,3,4,5,6-hexahydro-1-oxo-3-cyclopropylmethyl-8-hydroxy-6(eq)-ethyl-2,6-methano-3-benzazocine hydrochloride as an off-white solid which melted at 223°–226° C.

EXAMPLE 29

Proceeding in a manner similar to that described above in part A of Example 1, 14.7 g. of 1,2,3,4,5,6-hexahydro-1-oxo-8-hydroxy-6(eq)-ethyl-11(ax)-methyl-2,6-methano-3-benzazocine was interacted with 6.5 g. of cyclopropylmethyl bromide in the presence of 5.1 g. of sodium bicarbonate in 150 ml. of N,N-dimethylformamide to yield 3.7 g. of 1,2,3,4,5,6-hexahydro-1-oxo-3-cyclopropylmethyl-8-hydroxy-6(eq)-ethyl-11(ax)-methyl-2,6-methano-3-benzazocine as a white solid, m.p. 197°–199° C. The methanesulfonate salt of this base was a white solid, m.p. 208°–210° C. The (−)-cis isomer of the base, prepared by similar alkylation of the (−)-cis nor base was obtained as off-white crystals, m.p. 196°–198° C., $[\alpha]_D^{25} = -86.4°$ (2% in glacial acetic acid). The (+)-cis isiomer had m.p. 193°–199° C. and $[\alpha]_D^{25} = +89°$ (2% in glacial acetic acid). The racemic hydrochloride salt melted at 280°–282° C.

EXAMPLE 30

A. Following a procedure similar to that described above in Example 19, 48.4 g. of 1,2,3,4,5,6-hexahydro-8-methoxy-6(eq)-ethyl-11(eq)-methyl-2,6-methano-3-benzazocine methanesulfonate in 750 ml. of dilute sulfuric acid was oxidized by treatment with a solution of 19.8 g. of chromium trioxide in 750 ml. of dilute sulfuric acid. From the reaction mixture, after making it basic by addition of ammonium hydroxide, there was isolated 28.1 g. of crude 1,2,3,4,5,6-hexahydro-1-oxo-8-methoxy-6(eq)-ethyl-11(eq)-methyl-2,6-methano-3-benzazocine. This product was converted to the hydrochloride, a crystalline solid which after purification weighed 21.9 g.

B. By hydrolysis with 220 g. of 48% hydrobromic acid and basifying the hydrolysis product with ammonium hydroxide, 21.9 g. of 1,2,3,4,5,6-hexahydro-1-oxo-8-methoxy-6(eq)-ethyl-11(eq)-methyl-2,6-methano-3-benzazocine hydrochloride was converted to 5.5 g. of 1,2,3,4,5,6-hexahydro-1-oxo-8-hydroxy-6(eq)-ethyl-11(eq)-methyl-2,6-methano-3-benzazocine, a tan solid which melted at 264°-266° C.

C. Proceeding in a manner similar to that described above in Example 1, 10.0 g. of 1,2,3,4,5,6-hexahydro-1-oxo-8-hydroxy-6(eq)-ethyl-11(eq)-methyl-2,6-methano-3-benzazocine was interacted with 5.4 g. of cyclopropylmethyl bromide in the presence of 3.5 g. of sodium bicarbonate in 100 ml. of N,N-dimethylformamide. After the reaction mixture was acidified by treatment with ethereal hydrogen chloride, there was isolated 1.4 g. of 1,2,3,4,5,6-hexahydro-1-oxo-3-cyclopropylmethyl-8-hydroxy-6(eq)-ethyl-11(eq)-methyl-2,6-methano-3-benzazocine hydrochloride as a light orange solid which melted at 258°-260° C.

EXAMPLE 31

A. Proceeding in a manner similar to that described above in Example 19, 44.4 g. of 1,2,3,4,5,6-hexahydro-8-methoxy-6(eq),11(ax)-diethyl-2,6-methano-3-benzazocine in 600 ml. of dilute sulfuric acid was oxidized by treatment with a solution of 16.0 g. of chromium trioxide in 600 ml. of dilute sulfuric acid. From the reaction mixture, after making it basic by addition of ammonium hydroxide, there was isolated 32.6 g. of crude 1,2,3,4,5,6-hexahydro-1-oxo-8-methoxy-6(eq),11(ax)-diethyl-2,6-methano-3-benzazocine. A small sample of this product was recrystallized from ethyl alcohol to yield a white solid, m.p. 159°-162° C.

B. After refluxing 17.1 g. of 1,2,3,4,5,6-hexahydro-1-oxo-8-methoxy-6(eq),11(ax)-diethyl-2,6-methano-3-benzazocine hydrochloride with 200 ml. of 48% hydrobromic acid and basifying the resulting mixture with ammonium hydroxide there was obtained 12.7 g. of 1,2,3,4,5,6-hexahydro-1-oxo-8-hydroxy-6(eq),11(ax)-diethyl-2,6-methano-3-benzazocine as a pale pink solid which melted at 247°-251° C.

C. Using a procedure similar to that described above Example 1, 8.0 g. of 1,2,3,4,5,6-hexahydro-1-oxo-8-hydroxy-6(eq),11(ax)-diethyl-2,6-methano-3-benzazocine was interacted with 4.1 g. of cyclopropylmethyl bromide in the presence of 2.6 g. of sodium bicarbonate in 80 ml. of N,N-dimethylformamide to yield 4.7 g. of 1,2,3,4,5,6-hexahydro-1-oxo-3-cyclopropylmethyl-8-hydroxy-6(eq),11(ax)-diethyl-2,6-methano-3-benzazocine as a tan solid which melted at 208°-212° C. The methanesulfonate salt, which was prepared from the base and methanesulfonic acid and purified by washing with acetone, melted at 164°-165° C.

EXAMPLE 32

A. A solution of benzyl iodide in acetone was prepared from benzyl chloride (823 g.) and sodium iodide (975 g.). 3-Methyl-4-propylpyridine (879 g.) was added and the mixture was stirred at room temperature. Crystallization of the product from acetone-isopropyl acetate afforded 1-benzyl-3-methyl-4-propylpyridinium iodide in two crops (1334 g. and 162 g.), which melted at 94°-95° C.

1-Benzyl-3-methyl-4-propylpyridinium iodide (706.5 g.) was added to the Grignard reagent prepared from magnesium (147 g. of turnings and 147 g. of powder), p-anisyl chloride (630 g.) and ether (9,900 ml.), and the mixture was stirred overnight at room temperature. A solution of ammonium chloride (200 g.) in water (2,400 ml.) was added with stirring. The ether layer was separated and the aqueous layer was extracted with ether. Ether was removed from the combined ether layers, and the residual oil was dissolved in methanol (2,700 ml.). A solution of sodium borohydride (57 g.) in water (280 ml.) was added and the mixture was stirred overnight at room temperature. Methanol was removed, water was added, and the mixture was extracted three times with ether. The ether extracts were extracted with aqueous (1300 ml. water) phosphoric acid (200 g., 122 ml.). The phosphoric acid extract was basified with aqueous sodium hydroxide and extracted three times with ether. The ether extracts were dried and stripped of ether. A solution of oxalic acid (93 g.) in acetone (2,600 ml.) was added to the residual oil, affording crystalline 1-benzyl-2-(p-methoxybenzyl)-3-methyl-4-propyl-1,2,5,6-tetrahydropyridine oxalate (363 g.), which melted at 138°-140° C. Product recrystallized from ethanol melted at 147°-149° C.

A mixture of 1-benzyl-2-(p-methoxybenzyl)-3-methyl-4-propyl-1,2,5,6-tetrahydropyridine oxalate (377 g.), palladium-on-carbon (10%, 10.0 g.) and ethanol (to make 4,500 ml.) was hydrogenated for thirty minutes under pressure (about 50 p.s.i.g.), then filtered. The filtrate was concentrated, affording 2-(p-methoxybenzyl)-3-methyl-4-propyl-1,2,5,6-tetrahydropyridine oxalate in two crops (196 g. and 35 g.), which melted at 146°-147° C.

A mixture of 2-(p-methoxybenzyl)-3-methyl-4-propyl-1,2,5,6-tetrahydropyridine oxalate (200 g.) and hydrobromic acid (62%, 1,200 ml.) was heated under reflux for sixteen hours. Aqueous ammonia was added and the mixture was extracted with benzene. The benzene extract was washed with aqueous ammonia and stripped of benzene. Crystallization of the residue from acetone (1.5 l.) afforded 6(eq)-propyl-11(ax)-methyl-8-hydroxy-1,2,3,4,5,6-hexahydro-2,6-methano-3-benzazocine (33 g.), which melted at 217°-219° C. Recrystallization from aqueous N,N-dimethylformamide afforded product melting at 218.0–221.0° C. Further recrystallization from methanol afforded product melting at 220°-224° C.

Acetylation of 6(eq)-propyl-11(ax)-methyl-8-hydroxy-1,2,3,4,5,6-hexahydro-2,6-methano-3-benzazocine (21 g.) twice with acetic anhydride afforded 3-acetyl-6(eq)-propyl-11(ax)-methyl-8-acetoxy-1,2,3,4,5,6-hexahydro-2,6-methano-3-benzazocine as an oil (29.8 g.). A solution of the oil, sodium hydroxide (3.4 g.), ethanol (95%, 55 ml) and water (10 ml.) was heated under reflux for two hours, then concentrated. The residue was partitioned between ethyl acetate and dilute hydrochloric acid. The ethyl acetate layer was washed with water, dried and stripped of ethyl acetate, affording 3-acetyl-6(eq)-propyl-11(ax)-methyl-8-hydroxy-1,2,3,4,5,6-hexahydro-2,6-methano-3-benzazocine as an oil (26.6 g.). Dimethylsulfate (425 ml.) was added dropwise to a solution of the oil (24.5 g.) and aqueous sodium hydroxide (1 N, 170 ml.), and the mixture was stirred at room temperature for four hours, then extracted with chloroform. The chloroform extract was washed with aqueous sodium hydroxide, dried and concentrated. After unsuccessful attempts to purify the resulting oil (31 g.), including an attempt to remove the 3-acetyl from part of the product by hydrolysis with dilute hydrochloric acid, the product was reacetylated twice with acetic anhydride. Hydrolysis of the resulting oil (9.7 g.) in water (33 ml.) and concentrated hydrochloric acid (16 ml.) at reflux for twenty-three hours afforded in the aqueous phase after extraction with ether crystals of 6(eq)-propyl-11(ax)-methyl-8-methoxy-1,2,3,4,5,6-hexahydro-2,6-methano-3-benzazocine hydrochloride (5.8 g.) melting at 120°–135° C. with decomposition.

A mixture of 6(eq)-propyl-11(ax)-methyl-8-methoxy-1,2,3,4,5,6-hexahydro-2,6-methano-3-benzazocine hydrochloride (5.6 g.), chromium trioxide (2.5 g.) and sulfuric acid (19 ml.) diluted with water (to 190 ml.) was heated at steam bath temperature for two hours, basified with aqueous ammonia and extracted twice with ether. The ether extracts were dried and concentrated, and the solid (3.7 g.) was washed with hexane, affording 1-oxo-6(eq)-propyl-11(ax)-methyl-8-methoxy-1,2,3,4,5,6-hexahydro-2,6-methano-3-benzazocine (3.4 g.), which melted at 116°–119° C.

B. A mixture of 1-oxo-6(eq)-propyl-11(ax)-methyl-8-methoxy-1,2,3,4,5,6-hexahydro-2,6-methano-3-benzazocine (3.3 g.) and hydrobromic acid (48%, 35 ml.) was stirred under reflux for three hours, then concentrated. After unsuccessful attempts to purify the product, it was again heated at reflux with hydrobromic acid (48%, 25 ml.), and the resulting mixture was concentrated. The residue was washed with ethyl acetate (2.8 g.) and recrystallized, affording 1-oxo-6(eq)-propyl-11(ax)-methyl-8-hydroxy-1,2,3,4,5,6-hexahydro-2,6-methano-3-benzazocine hydrobromide (2.0 g.), which melted at 244°–248° C.

C. A mixture of 1-oxo-6(eq)-propyl-11(ax)-methyl-8-hydroxy-1,2,3,4,5,6-hexahydro-2,6-methano-3-benzazocine hyrobromide (1.9 g.), sodium bicarbonate (1.5 g.), N,N-dimethylformamide (20 ml.) and cyclopropylmethyl bromide (0.9 g.) was stirred under reflux for four hours, then concentrated. The residue was partitioned between chloroform and water. The chloroform layer was dried and concentrated. Hexane and ether were added to the residue and the resulting solid (1.0 g.) was recrystallized, first from ethyl acetate-isopropyl alcohol and then from ethanol-N,N-dimethylformamide, affording white crystals of 1,2,3,4,5,6-hexahydro-1-oxo-3-cyclopropylmethyl-8-hydroxy-6(eq)-propyl-11(ax)-methyl-2,6-methano-3-benzazocine (0.4 g.), which melted at 229°–232° C.

EXAMPLE 33

A. Dimethylsulfate (4.0 g.) was added dropwise to a mixture of 1,2,3,4,5,6-hexahydro-3-benzyl-8-hydroxy-6(eq)-methyl-11(ax)-ethyl-2,6-methano-3-benzazocine (prepared by the method of U.S. Pat. No. 3,585,203; described in British Pat. No. 1,431,712). The clear solution was diluted with water and extracted with hexane. The hexane extract was washed with aqueous sodium hydroxide (1 N) and water, dried and stripped of hexane, affording 1,2,3,4,5,6-hexahydro-3-benzyl-8-methoxy-6(eq)-methyl-11(ax)-ethyl-2,6-methano-3-benzazocine (14 g.), the hydrochloride salt of which was prepared.

A mixture of 1,2,3,4,5,6-hexahydro-3-benzyl-8-methoxy-6(eq)-methyl-11(ax)-ethyl-2,6-methano-3-benzazocine hydrochloride (14 g.), ethanol (700 ml.) and palladium-on-carbon (about 50 mg.) was hydrogenated for four hours at 60° C., then filtered. The filtrate was concentrated. Crystallization of the residue from ethyl acetate afforded 1,2,3,4,5,6-hexahydro-8-methoxy-6(eq)-methyl-11(ax)-ethyl-2,6-methano-3-benzazocine hydrochloride.

A mixture of 1,2,3,4,5,6-hexahydro-8-methoxy-6(eq)-methyl-11(ax)-ethyl-2,6-methano-3-benzazocine hydrochloride (7.0 g.), chromium trioxide (3.3 g.) and aqueous sulfuric acid (5 M, 80 ml.) was stirred at room temperature for two hours, then at steam bath temperature for one-half hour, and neutralized with concentrated aqueous ammonia (20 ml.). Ether was added and the mixture was filtered. The ether layer was separated, dried and concentrated. The resulting oil (6.2 g.) crystallized and part of it was recrystallized from cyclohexane, affording 1,2,3,4,5,6-hexahydro-1-oxo-8-methoxy-6(eq)-methyl-11(ax)-ethyl-2,6-methano-3-benzazocine, which melted at 81°–83° C. and whose hydrochloride salt, prepared from the base and hydrochloric acid, melted at 238°–240° C.

B. A mixture of 1,2,3,4,5,6-hexahydro-1-oxo-8-methoxy-6(eq)-methyl-11(ax)-ethyl-2,6-methano-3-benzazocine (6 g.) and aqueous hydrobromic acid (48%, 25 ml.) was heated under reflux for three hours, then concentrated. Basification of an aqueous solution of the residue with sodium bicarbonate and recrystallization of the resulting product from ethanol afforded 1,2,3,4,5,6-hexahydro-1-oxo-8-hydroxy-6(eq)-methyl-11(ax)-ethyl-2,6-methano-3-benzazocine (3.7 g.), which did not melt when heated to 270° C.

C. A mixture of 1,2,3,4,5,6-hexahydro-1-oxo-8-hydroxy-6(eq)-methyl-11(ax)-ethyl-2,6-methano-3-benzazocine (2.0 g.), cyclopropylmethyl bromide (1.2 g.), sodium bicarbonate (0.7 g.) and N,N-dimethylformamide (20 ml.) was stirred at room temperature for twenty hours then at 80° C. for two hours, then concentrated. An ether solution of the residue was washed with water, dried, treated with charcoal, filtered, and concentrated. Crystallization of the residue from ethyl acetate and recrystallization of part of the product (2.2 g.) from ethyl acetate afforded 1,2,3,4,5,6-hexahydro-1-oxo-3-cyclopropylmethyl-8-hydroxy-6(eq)-methyl-11(ax)-ethyl-2,6-methano-3-benzazocine, which melted at 208°–211° C.

D. A mixture of 1,2,3,4,5,6-hexahydro-1-oxo-8-methoxy-6(eq)-methyl-11(ax)-ethyl-2,6-methano-3-benzazocine hydrochloride (35.9 g.), cyclopropylmethyl bromide (19.7 g.), sodium bicarbonate (24.6 g.) and N,N-dimethylformamide (400 ml.) was stirred under reflux for seven hours, then concentrated. The residue was partitioned between ethyl acetate and aqueous ammonia. The ethyl acetate layer was washed with water, then saturated aqueous sodium chloride, treated with charcoal, filtered, and stripped of ethyl acetate, affording 1,2,3,4,5,6-hexahydro-1-oxo-3-cyclopropylmethyl-8-methoxy-6(eq)-methyl-11(ax)-ethyl-2,6-methano-3-benzazocine (36.5 g.).

E. Propylthiol (53.5 ml.) was added dropwise with stirring to a mixture of 1,2,3,4,5,6-hexahydro-1-oxo-3-cyclopropylmethyl-8-methoxy-6(eq)-methyl-11(ax)-ethyl-2,6-methano-3-benzazocine (36.5 g.), N,N-dimethylformamide (750 ml.) and sodium hydride (50% oil dispersion, 28.0 g.) under nitrogen. The resulting mixture was heated under reflux for three hours, diluted with water (1 l.), washed with hexane (2×600 ml.), acidified with aqueous hydrochloric acid (6 N), washed again with hexane (2×600 ml.), basified with aqueous ammonia, and extracted with ethyl acetate (4×400 ml.). The combined ethyl acetate extracts were washed with water, then saturated aqueous sodium chloride, treated with charcoal, and stripped of ethyl acetate. Crystallization of the residue (15 g.) from ethanol and recrystallization of part (2.5 g.) of the first crop (8.0 g.) from ethyl acetate afforded 1,2,3,4,5,6-hexahydro-1-oxo-3-cyclopropylmethyl-8-hydroxy-6(eq)-methyl-11-(ax)-ethyl-2,6-methano-3-benzazocine, which melted at 207°-209° C. Treatment of the base with methanesulfonic acid and crystallization of the product from methanol-ether afforded the methanesulfonate salt, which melted at 216°-217° C.

EXAMPLE 34

A mixture of 1,2,3,4,5,6-hexahydro-1-oxo-8-hydroxy-6(eq),11(ax)-dimethyl-2,6-methano-3-benzazocine (9.2 g.), 2-phenylethylbromide (9.2 g.), sodium bicarbonate (3.4 g.) and N,N-dimethylformamide (100 ml.) was stirred at steam bath temperature, then concentrated. The residue was partitioned between ether (200 ml.) and water (200 ml.). The ether layer was washed with water, then saturated aqueous sodium chloride, dried, treated with charcoal, filtered and stripped of ether. After initial unsuccessful attempts to purify the resulting solid (9.9 g.) from methanol, the several crops and mother liquors were combined, evaporated to dryness (9.0 g.) and again crystallized from methanol. A chloroform solution of the product (4.8 g.) was chromatographed on silica gel (240 ml.). Recrystallization from ethanol of the fractions of eluted crystalline solid (2.4 g.) which were shown to be pure by thin layer chromatography afforded 1,2,3,4,5,6-hexahydro-1-oxo-3-(2-phenylethyl)-8-hydroxy-6(eq),11(ax)-dimethyl-2,6-methano-3-benzazocine (1.8 g.), which melted at 190°-192° C.

EXAMPLE 35

A. A mixture of 1,2,3,4,5,6-hexahydro-8-methoxy-6(eq),11(ax)-dimethyl-2,6-methano-3-benzazocine (15.0 g.), chloroform (225 ml.), triethylamine (21.6 ml.) and cyclobutanecarbonyl chloride (7.8 g.) was stirred overnight at room temperature, washed with water, then aqueous hydrochloric acid (1 N), then water again, dried, filtered, and concentrated, affording 1,2,3,4,5,6-hexahydro-3-cyclobutanecarbonyl-8-methoxy-6(eq),1-1(ax)-dimethyl-2,6-methano-3-benzazocine (19.8 g.).

A mixture of 1,2,3,4,5,6-hexahydro-3-cyclobutanecarbonyl-8-methoxy-6(eq),11(ax)-dimethyl-2,6-methano-3-benzazocine (19.8 g.), ether (300 ml.) and lithium aluminum hydride (2.4 g.) was allowed to reflux gently, then stirred overnight at room temperature. Water (10 ml.) and aqueous sodium hydroxide (3 N, 3 ml.) were added, the mixture was filtered, and the filter cake was washed with ether. The filtrate was concentrated. Hydrogen chloride was added to a solution of the residue (17.2 g.) in acetone, and the resulting solid was washed with acetone, then ether, affording 1,2,3,4,5,6-hexahydro-3-cyclobutylmethyl-8-methoxy-6(eq),11(ax)-dimethyl-2,6-methano-3-benzazocine hydrochloride (16.3 g.), which melted at 200°-203° C.

A mixture of 1,2,3,4,5,6-hexahydro-3-cyclobutylmethyl-8-methoxy-6(eq),11(ax)-dimethyl-2,6-methano-3-benzazocine hydrochloride (16.2 g.), chromium trioxide (6.6 g.) and aqueous sulfuric acid (45 ml. of concentrated acid diluted to 500 ml. with water) was stirred at steam bath temperature for two hours, basified with aqueous ammonia, and extracted with ether (3×300 ml.). The combined ether extracts were filtered, washed first with water and then with saturated aqueous sodium chloride, dried, filtered and stripped of ether. The residue (14.3 g.) was chromotographed in three portions on silica gel (125 g. for each portion), affording 1,2,3,4,5,6-hexahydro-1-oxo-3-cyclobutylmethyl-8-methoxy-6(eq),11(ax)-dimethyl-2,6-methano-3-benzazocine in three portions (4.2 g., 3.8 g., 3.3 g.).

B. Propylthiol (13.0 ml.) was added dropwise with stirring to a mixture of 1,2,3,4,5,6-hexahydro-1-oxo-3-cyclobutylmethyl-8-methoxy-6(eq),11(ax)-dimethyl-2,6-methano-3-benzazocine (11.3 g.), N,N-dimethylformamide (200 ml.) and sodium hydride (50% oil dispersion, 6.9 g.) under nitrogen. The resulting mixture was heated under reflux for three hours, diluted with water (300 ml.), washed with pentane, acidified with methanesulfonic acid, washed again with pentane, basified with aqueous ammonia, and extracted with butanol. The butanol extract was washed with water, dried, filtered, and concentrated. A methanol solution of the residue was chromatographed on silica gel (650 ml.). The column was eluted with methanol (first fraction 400 ml., 100-ml. fractions thereafter). After an unsuccessful attempt to purify the residue of the third (5.5 g.) and fourth (3.3 g.) fractions as the methanesulfonate salt, the salt was basified and recrystallized from ethyl acetate, affording 1,2,3,4,5,6-hexahydro-1-oxo-3-cyclobutylmethyl-8-hydroxy-6(eq),11(ax)-dimethyl-2,6-methano-3-benzazocine (4.6 g.), which melted at 196°-197° C.

EXAMPLE 36

A mixture of 1,2,3,4,5,6-hexahydro-1-oxo-8-hydroxy-6(eq)-ethyl-11(ax)-methyl-2,6-methano-3-benzazocine (4.9 g.), propyl iodide (4.1 g.), sodium bicarbonate (1.7 g.) and N,N-dimethylformamide (50 ml.) was stirred at steam bath temperature for two hours, then diluted with water (250 ml.). Treatment of a methanol solution of the product (4.3 g.) with methanesulfonic acid (1.5 g.) and recrystallization of the product from methanol-ether afforded 1,2,3,4,5,6-hexahydro-3-propyl-1-oxo-8-hydroxy-6(eq)-ethyl-11(ax)-methyl-2,6-methano-3-benzazocine methanesulfonate (3.1 g.), which melted at 219°-220° C.

EXAMPLE 37

A mixture of 1,2,3,4,5,6-hexahydro-1-oxo-8-hydroxy-6(eq)-ethyl-11(ax)-methyl-2,6-methano-3-benzazocine, allyl bromide (2.9 g.), sodium bicarbonate (1.7 g.) and N,N-dimethylformamide (50 ml.) was stirred at steam bath temperature for two hours, then diluted with water (250 ml.). Two recrystallizations of the product (5.1 g.) from methanol afforded 1,2,3,4,5,6-hexahydro-3-allyl-1-oxo-8-hydroxy-6(eq)-ethyl-11(ax)-methyl-2,6-methano-3-benzazocine (2.2 g.), which melted at 184°-185° C.

BIOLOGICAL TEST RESULTS

As stated above the compounds of Formula I are useful as analgesics and mostly also useful as narcotic antagonists as shown by tests in experimental animals. As presumptive tests of analgesia the anti-acetylcholine writhing, anti-phenylquinone writhing, anti-bradykinin and EDTA anti-nociceptive tests are carried out as follows:

Anti-acetylcholine Writhing Test

An intraperitoneal injection of acetylcholine, 3.2 mg./kg., causes mice to exhibit a response consisting of abdominal constriction, and sometimes twisting, followed by extension of the hind limbs. This response has also been called writhing. Animals are pretreated with test compounds (20 minutes for both subcutaneous and oral routes) and observed for two minutes immediately following the administration of acetylcholine. Mice not responding during the two-minute observation period are scored protected while those responding one or more times are scored not protected. Test compounds are screened at doses of 75 and 25 mg./kg. subcutaneously or 150 and 50 mg./kg. orally. The standard injection volume for test compounds is 10 ml./kg. ED50 values for active compounds are estimated by probit analysis of quantal scores for 4 or more dosage levels using 15 animals per dose. Vehicle-pretreated control animals are tested concurrently with each run of 15 experimental animals.

Anti-phenylquinone Writhing Test

This test is used to confirm the anti-acetylcholine writhing test. The ability of compounds to prevent phenyl-p-quinone (phenylquinone)-induced writhing in mice is determined in this test. An intraperitoneal injection of phenylquinone, 3.0 mg./kg., causes mice to exhibit the same writhing response as does acetylcholine as described above. Animals are pretreated with test compounds (15 minutes for subcutaneous route, 30 minutes for oral route) and observed for three one-minute intervals during the 5–12 minutes following administration. Mice responding fewer than three times during the three one-minute observation periods are scored protected while those responding three or more times are scored not protected. Test compounds are screened using 10–14 animals per treatment, usually at doses of 75–100 mg./kg. subcutaneously or 150–200 mg./kg. orally. The standard injection volume for test compounds is 10 ml./kg. ED50 values for active compounds are estimated by probit analysis of quantal scores for 3–5 dosage levels using 14–30 animals per dose. Vehicle-pretreated control animals are tested daily.

Anti-bradykinin Test

This is a secondary evaluation of analgesic activity. Rats prepared surgically under ether anesthesia with an indwelling intra-carotid cannula exhibit a response to bradykinin injections consisting of ipsilateral head rotation and front paw flexion. The threshold dose of bradykinin required for production of the response is determined for each animal, and is readministered at fixed intervals during a two-hour period following the subcutaneous or oral administration of test compounds. In the control response marked rotation of the head and flexion of the forepaw are each scored +2, for a total response score (TRS) of +4. For post-medication scoring any decrease in head rotation or paw flexion from control is each scored +1, rather than +2, while no movement of either the head or paw is each scored 0. Therefore, the TRS following any bradykinin challenge can vary from 0 to 4. Animals whose TRSs are 0-0, 0-+1 or +1-0 after any two consecutive bradykinin challenges during the two-hour post-medication period are scored protected. Compounds are screened using 5 animals per treatment, usually at 100 mg./kg. subcutaneously or 200 mg./kg. orally. The standard injection volume for test compounds is 2 ml./kg. for both subcutaneous and oral medication. ED50 values of active compounds are estimated by probit analysis of quantal scores from 4 or more dosage levels using 5 animals per dose. In addition the average TRSs obtained at each test interval with each treatment are plotted to permit examination of time-effect relationships and to provide a rough expression of drug effect using graded data. A vehicle-pretreated control animal is tested daily. Synthetic bradykinin from Sandoz Pharmaceuticals is diluted with saline to the proper concentrations for determination of threshold doses for producing the response. All bradykinin injections are made at a constant volume of 0.2 ml. per rat.

EDTA Antinociceptive Test

This is also a secondary evaluation of analgesic activity. The test animal is the guinea pig. A threshold intradermal dose of ethylenediaminetetraacetic acid (EDTA) which can reproducibly elicit a cumulative response score of 12–18 discrete episodes of jumping, rearing, running, vocalization and biting or scratching at the site of injection within 40 seconds after challenge is determined for each animal. Thirty minutes after the administration of saline or test compound to 6–7 animals per dose, each animal is again challenged with its own threshold dose of EDTA. An effective drug dose is considered to be one which reduces the response score to 6 or less.

The test used for narcotic antagonism is the tail-flick test, which is also used to test for narcotic agonism, as follows:

Tail-flick Agonist Test

Rats normally respond to a thermal stimulus applied to the tail by flicking their tails out from under the heat source. The intensity of the stimulus utilized is one which produces control response-times (CRT) of 2–4 seconds. Experimental response-times (ERT) are determined 30 minutes after subcutaneous injections and 60 minutes after oral medications. The stimulus is terminated if animals did not respond after an exposure of 20 seconds. Therefore, the maximum possible increase (MPI) in response-time for any given animal is 20 minus the CRT. The average percent effect, or percent of the maximum possible increase (%MPI) obtained after any given test compound treatment is calculated by the formula $$\%MPI = \frac{\text{Average } ERT - \text{Average } CRT}{20 - \text{Average } CRT} \times 100.$$

Test compounds are screened using 6 animals per treatment usually at 120 mg./kg. subcutaneously or 200 mg./kg. orally. The standard injection volume for test compounds is 1.0 ml./kg. subcutaneously and 10 ml./kg. orally. ED50 or ED80 values of active compounds are obtained by the Miller and Tainter [Proc. Soc. Exptl. Biol., N.Y., 57:261 (1944)] method of probit analysis of data from at least 3 dosage levels using 18 animals per treatment.

Tail-flick Antagonist Test

The rat tail-flick test is also used to determine whether compounds have narcotic antagonist activity. Animals are pretreated (10 minutes for subcutaneous route, 20 minutes for oral route) with test compounds and are then given subcutaneously a standard ED80 dose of phenazocine (as the hydrobromide, 0.5 mg./kg.) or meperidine (as the hydrochloride, 60 mg./kg.) or a standard ED90 dose of morphine (as the sulfate, 15 mg./kg.). Active compounds reduce, in a dose-dependent manner, and can completely block, the agonist effect of all narcotics. The average percent antagonist effect produced by any given treatment is calculated by the formula $$\% \text{ antagonism} = 100 - \frac{\%MPI \text{ of narcotic} + \text{test drug}}{0.80}.$$

Test compounds are screened using 6 animals per treatment, usually at 80 mg./kg. subcutaneously or 200 mg./kg. orally. The standard injection volume for test compounds is 1.0 ml./kg. subcutaneously and 10 ml./kg. orally. AD50 values of active compounds are obtained from Litchfield-Wilcoxon [J. Pharm. Exptl. Therap., 96:99 (1944)] plots of data from at least 3 dosage levels using 18 animals per treatment.

The compounds of Formula I are active in the foregoing anti-acetylcholine writhing test as shown by the following results:

Anti-acetylcholine Writhing Test Results

| Product of Example | Subcutaneous ED50 Expressed in Mg./Kg. of Base (95% Confidence Limits) |
|---|---|
| 1$^a$ | 0.16(0.12–0.21) |
| 1$^b$ | 0.12(0.09–0.15) |
| 1$^c$ | 0.16(0.14–0.19) |
| 2$^a$ | 0.14(0.11–0.17) |
| 4 | 0.14(0.11–0.22) |
| 5 | 0.06(0.02–0.12) |
| 6 | 0.09(0.06–0.13) |
| 7 | 0.06(0.14–0.09) |
| 8 | 0.08(0.05–0.11) |
| 9 | 0.07(0.05–0.11) |
| 10 | 0.10(0.05–0.14) |
| 11 | 0.10(0.06–0.18) |
| 12 | 0.06(0.04–0.09) |
| 13 | 0.05(0.02–0.10) |
| 15 | 3.2(2.6–3.7) |
| 16 | 1.5(0.8–2.5) |
| 17 | 4.8(2.6–7.4) |
| 18 | 10(9.3–12) |
| 26C$^c$ | 0.11(0.09–0.14) |
| 27 | 30(18–50) |
| 28C | 0.38(0.23–0.54) |
| 29$^b$ | 0.045(0.029–0.059) |
| 30C | 2.1(1.0–3.7) |
| 31C$^c$ | 0.15(0.11–0.2) |
| 32C | 1.5(0.6–3.8) |
| 33E | 0.47(0.32–0.80) |
| 34 | 4.2(3.1–6.1) |
| 35B | 3.9(2.8–5.3) |
| 36 | 1.0(0.72–1.5) |
| 37 | 2.3(2.1–3.8) |

$^a$hydrochloride salt
$^b$base
$^c$methanesulfonate salt

The product of Example 3 was tested subcutaneously at 0.1, 1., 10 and 100 mg./kg. and showed 20, 27, 7 and 47% effects, respectively, which were insufficient to calculate an ED50 value. The product of Example 26D (methanesulfonate salt) was tested subcutaneously and showed a 33% effect at 25 mg./kg. and a 93% effect at 75 mg./kg.

The compounds of Formula I are mostly also active as narcotic antagonists and inactive as agonists in the foregoing tail-flick test as shown by the following results:

Tail-Flick Antagonist Test Results

| | Subcutaneous AD50 Expressed in Mg./Kg. of Base (95% Confidence Limits) Against | | |
|---|---|---|---|
| Product of Example | Phenazocine | Meperidine | Morphine |
| 1$^a$ | 4.3(2.6–7.1) | 2.0(1.1–3.6) | 4.0(2.6–6.1) |
| 2$^b$ | 3.0(1.9–4.8) | | |
| 3 | 6.0(4–8.7) | | |
| 4 | 6.2(3.6–10.5) | | |
| 5 | 38(21–68) | | |
| 6 | 7.0(4.0–12) | | |
| 7 | 5.2(2.9–9.4) | | |
| 9 | 14(9.0–23) | | |
| 15 | 2.8(1.8–4.3) | | |
| 16 | 2.2(1.3–3.7) | | |
| 17 | | 0.98(0.5–1.9) | |
| 18 | | 11 (flat curve) | |
| 26C$^d$ | 2.4(1.4–4.1) | | |
| 27 | 2.8(1.5–5.3) | | |
| 28C | 14(8.5–23) | | |
| 30C | 4.2(2.4–7.1) | | |
| 31C$^d$ | 0.48(0.27–0.86) | | |
| 33E | 0.17(0.09–0.32) | | |
| 36 | 6.2(3.6–11) | | |
| 37 | 6.3(3.9–10) | | |

$^a$lactic acid solution of free base
$^b$hydrochloride salt
$^c$base
$^d$methanesulfonate salt The products of Examples 29, 34 and 35B are exceptions. The product of Example 29 is inactive as a narcotic antagonist but active as an agonist (ED50 9±10 mg./kg. subcutaneously). The products of Examples 34 and 35B are inactive as narcotic antagonists and weakly active as agonists (ED50 56±9.1 and 200±49 subcutaneously, respectively). The product of Example 26C is the levo-rotatory isomer of the product of Example 1. The product of Example 26D, which is the dextro-rotatory isomer of the product of Example 1 was inactive at 10 mg./kg. and showed a 32% effect at 80 mg./kg. subcutaneously (methanesulfonic salt) against phenazocine.

1,2,3,4,5,6-hexahydro-1-oxo-cyclopropylmethyl-8-hydroxy-6(eq), 11(ax)-dimethyl-2,6-methano-3-benzazocine, which is the product of Example 1 in its free base form, or an acid addition salt thereof, is a preferred species of Formula I and has been tested in all of the foregoing tests as shown by the following results, and in other biological tests in experimental animals, and is being tested in humans as an analgesic for moderate to severe pain.

Anti-acetylcholine Writhing Test Results

| ED50 Expressed in Mg./Kg. of Base (95% Confidence Limits) | |
|---|---|
| Subcutaneous | Oral |
| 0.16(0.14–0.19) | 12(9.1–16) |

Anti-phenylquinone Writhing Test Results

| ED50 Expressed in Mg./Kg. of Base (95% Confidence Limits) | |
|---|---|
| Subcutaneous | Oral |
| 0.16(0.12–0.21) | 15.2(10–23) |

Anti-bradykinin Test Results

ED50 Expressed in Mg./Kg. of Base (95% Confidence Limits)

-continued

| Subcutaneous | Oral |
|---|---|
| 0.069(0.021–0.14) | 10(1.5–24) |

EDTA Anti-nociceptive Test result
Subcutaneous Effective Dose Expressed in Mg./Kg. of Base
0.03

Tail-flick Agonist Test Results
Percent Inhibition of Response Expressed in Mg./Kg. of Base

| Subcutaneous | Oral |
|---|---|
| 2.3% at 120; atoxia, decreased activity | 11.2% at 200; 1/6 dead; slight salivation, partial loss of righting reflex |

Tail-flick antagonist Test Results
$AD_{50}$ Expressed in Mg./Kg. of Base
(95% Confidence Limits) Against

| | Phenazocine | Meperidine | Morphine |
|---|---|---|---|
| Subcutaneous | 5.0(3.1–8.0) | 7.2(5.0–10) | 4.9(3.5–6.9) |
| Oral | 63(38–105) | 78(51–119) | 91(58–143) |

In summary of the foregoing test results, the product of Example 1 has a profile of strong analgesic activity together with weak narcotic antagonist activity.

Another preferred species of Formula I is 1,2,3,4,5,6-hexahydro-1-oxo-3-cyclopropylmethyl-8-hydroxy-6(eq)-ethyl-11(ax)-methyl-2,6-methano-3-benzazocine, which is the product of Example 29 in its free base form, or an acid addition salt thereof, and which has also been tested in all of the foregoing tests as shown by the following results, and in other tests in experimental animals in preparation for possible clinical testing.

Anti-acetylcholine Writhing Test Results
$ED_{50}$ Expressed in Mg./Kg. of Base (95%) Confidence Limits

| Subcutaneous | Oral |
|---|---|
| 0.074(0.058–0.093) | 7.6(6.4–8.9) |

Anti-phenylquinone Writhing Test Results
$ED_{50}$ Expressed in Mg./Kg. of Base (95% Confidence Limits)

| Subcutaneous | Oral |
|---|---|
| 0.03(0.02–0.06) | 9.1(6.4–4–12) |

Anti-bradykinin Test Results
$ED_{50}$ Expressed in Mg./Kg. of Base (95% Confidence Limits)

| Subcutaneous | Oral |
|---|---|
| 0.053(0.025–0.087) | 11(1.5–16) |

EDTA Anti-nociceptive Test Result
Subcutaneous Effective Dose Expressed in Mg./Kg. of Base
0.025

Tail-flick Agonist Test Result
Subcutaneous $ED_{50}$ Expressed in Mg./Kg. of Base
9.0 ± 10

Tail-flick antagonist Test Result
Inactive

In summary of the foregoing test results the product of Example 29 has a profile of strong analgesic activity together with weak narcotic antagonist activity and no narcotic activity.

In addition to having been tested in the foregoing tests the products of Examples 1 and 29 have also been tested in experimental animals for dependence, psychopharmacologic, cardiovascular and respiratory effects, metabolism and toxicity.

I claim:

1. 3-Q-6-$R^1$-11-$R^2$-1-$Y^1$-1-$Y^2$-8-Z-1,2,3,4,5,6-Hexahydro-2,6-methano-3-benzazocine having the structural formula

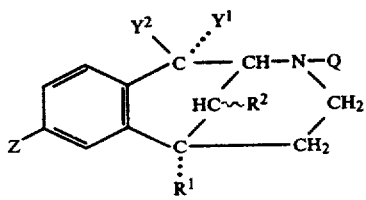

wherein:
Q is cyclopropylmethyl, cyclobutylmethyl, propyl, allyl or 2-phenylethyl;
$R^1$ is methyl, ethyl or propyl;
$R^2$ is hydrogen, methyl or ethyl;
$Y^1$ taken alone is hydrogen;
$Y^2$ taken alone is hydroxy; or
$Y^1$ and $Y^2$ taken together are oxo; and
Z is hydroxy; and when $Y^1$ and $Y^2$ taken together are oxo, Z is also acyloxy selected from the group consisting of acetoxy, propionyloxy, butyryloxy, pivalyloxy, isobutyryloxy, isovaleryloxy, 3,3-dimethylbutyanyloxy, benzoyloxy, p-anisoyloxy, m-anisoyloxy, p-toluyloxy and p-trifluoromethylbenzoyloxy;
or an acid-addition salt thereof.

2. A compound according to claim 1 wherein $Y^1$ and $Y^2$ taken together are oxo or an acid-addition salt thereof.

3. A compound according to claim 2 wherein Z is hydroxy or an acid-addition salt thereof.

4. A compound according to claim 3 wherein $R^2$ is axial methyl or an acid-addition salt thereof.

5. A compound according to claim 4 wherein Q is cyclopropylmethyl or an acid-addition salt thereof.

6. A compound according to claim 5 wherein $R^1$ is methyl or an acid-addition salt thereof.

7. A compound according to claim 6 wherein the acid-addition salt is the methanesulfonate.

8. A compound according to claim 5 wherein $R^1$ is ethyl or an acid-addition salt thereof.

9. A compound according to claim 8 wherein the acid-addition salt is the methanesulfonate.

10. 6-$R^1$-11-$R^2$-1-$Y^1$-1-$Y^2$-8-Z*-1,2,3,4,5,6-Hexahydro-2,6-methano-3-benzazocine having the structural formula

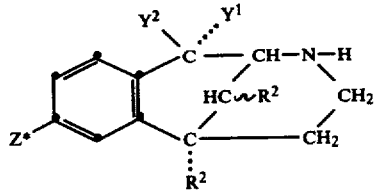

wherein:
$R^1$ is methyl, ethyl or propyl;
$R^2$ is hydrogen, methyl or ethyl;
$Y^1$ taken alone is hydrogen;
$Y^2$ taken alone is hydroxy; or
$Y^1$ and $Y^2$ taken together are oxo; and
Z* is hydroxy or methoxy;
or an acid-addition salt thereof.

11. A compound according to claim 10 wherein $Y^1$ and $Y^2$ taken together are oxo or an acid-addition salt thereof.

12. A compound according to claim 11 wherein $R^2$ is axial methyl or an acid-addition salt thereof.

13. A compound according to claim 12 wherein $R^1$ is methyl or an acid-addition salt thereof.

14. A compound according to claim 13 wherein $Z^*$ is hydroxy or an acid-addition salt thereof.

15. A compound according to claim 13 wherein $Z^*$ is methoxy or an acid-addition salt thereof.

16. A compound according to claim 12 wherein $R^1$ is ethyl or an acid-addition salt thereof.

17. A compound according to claim 16 wherein $Z^*$ is hydroxy or an acid-addition salt thereof.

18. A compound according to claim 16 wherein $Z^*$ is methoxy or an acid-addition salt thereof.

* * * * *